United States Patent [19]
Potapova et al.

[11] Patent Number: 6,033,073
[45] Date of Patent: Mar. 7, 2000

[54] VISUAL TRAINING SYSTEM AND APPARATUS FOR VISION CORRECTION, ESPECIALLY FOR VARIOUS FORMS OF STRABISMUS ("CROSSED" EYES)

[76] Inventors: Olga Potapova, 5950 E. Pratt St., Baltimore, Md. 21224; Yevgeniy (Eugueni) L. Mikhaylenok; Olga Voronina, both of Prospect Morisa Toreza 71/3-28, St. Petersburg, Russian Federation, 194214

[21] Appl. No.: 09/071,223
[22] Filed: May 1, 1998

Related U.S. Application Data

[60] Provisional application No. 60/055,859, Aug. 15, 1997.

[51] Int. Cl.$^7$ .................................................. A61B 3/10
[52] U.S. Cl. ............................................. 351/211; 600/26
[58] Field of Search .................................. 351/203, 205, 351/209, 211, 212, 237, 238; 600/26, 27, 28, 300

[56] References Cited

U.S. PATENT DOCUMENTS

| | | | |
|---|---|---|---|
| 4,533,221 | 8/1985 | Trachtman | 351/203 |
| 4,778,268 | 10/1988 | Randle | 351/203 |
| 4,896,959 | 1/1990 | O'Brien | 351/203 |
| 5,002,384 | 3/1991 | Trachtman | 351/203 |
| 5,363,154 | 11/1994 | Galanter et al. | 351/203 |
| 5,374,193 | 12/1994 | Trachtman | 434/258 |
| 5,518,497 | 5/1996 | Widjaja et al. | 600/27 |

OTHER PUBLICATIONS

Goldrich, S.G., "Oculomotor Biofeedback Therapy for Exotropia", Am.Journ.of Optometry & Physiological Optics, vol. 59, No. 4, pp. 306–317, 1982, United States.

*Primary Examiner*—George Manuel
*Attorney, Agent, or Firm*—Frank G. Morkunas

[57] ABSTRACT

A vision correction apparatus and system for correcting various forms of strabismus. The apparatus has a viewing mechanism for viewing images, a dynamic stimulus device to be engaged or disengaged depending on control signals generated from the apparatus, a measuring mechanism for observing and measuring viewing activity of the user, data storage mechanism for storing data measured by the measuring mechanism; and control mechanism for assessing stored data and, in relation to an assessment made of the stored data, for generating and transmitting a control signal to engage or disengage the dynamic stimulus device. The measuring mechanism further measures alpha, beta, and theta brain waves after viewing a structured and an unstructured image for a pre-determined period of time, observes and measures electrooculogram (EOG) patterns of each eye, and observes and measures interfering muscular movement but use of an electromyogram (EMG) after which the data obtained from the measurements is assessed by the control mechanism to establish individualized normalizing co-efficients and values, to establish brain visual activation function and value, to establish absolute differences between EOG patterns of the eyes, to account for interfering muscular movement not associated with EOG patterns, and to establish a trend which, if supportive of vision correction, engages the dynamic stimulus device and, if not supportive of vision correction, disengages the dynamic stimulus device thereby encouraging a user to self-correct by repeating activity which engages the dynamic stimulus device.

33 Claims, 29 Drawing Sheets

| Frequency Band | Normalized Power Spectrum Estimate (%) | | Individual Normalizing Coefficient k |
|---|---|---|---|
| | Unstructured Image (50) | Structured Image (54) | |
| θ | 39 | 49 | 49/39=1.26 kθ (5) |
| α | 48 | 33 | 33/48=0.69 kα(3) |
| β | 13 | 18 | 18/13=1.38 kβ(4) |

$$A = \frac{(1.26 \times \theta) \times (1.38 \times \beta)}{(0.69 \times \alpha)}$$

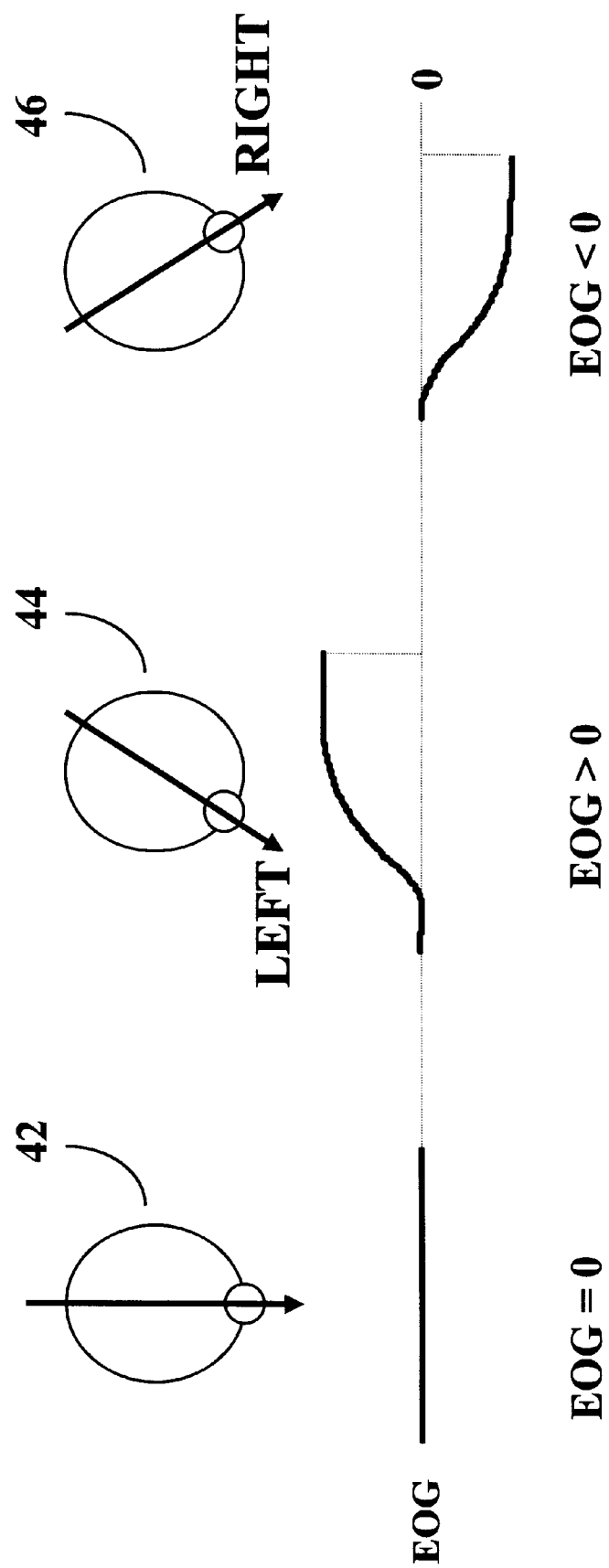

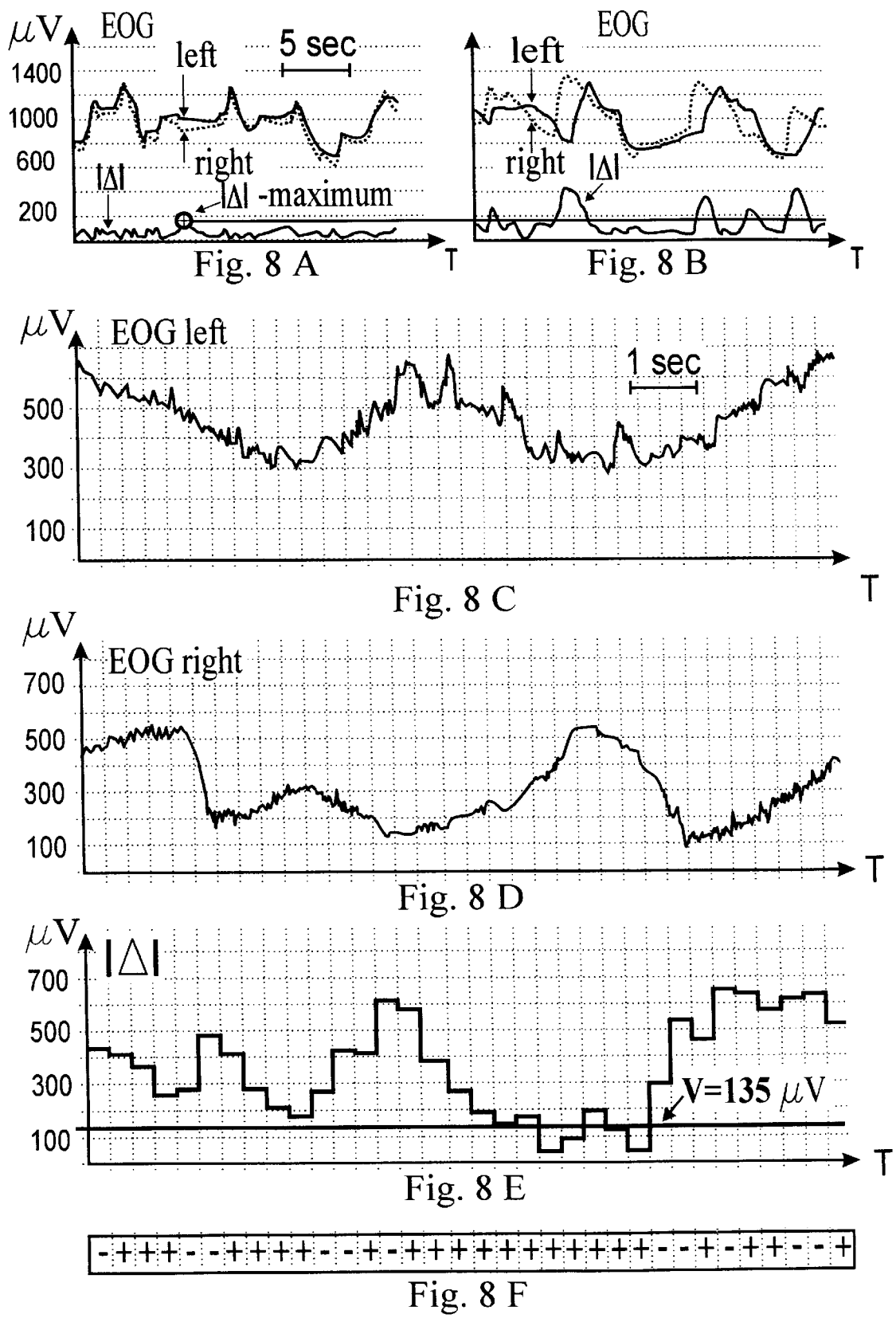

PATIENT [RICHARD LEONARD] SESSION [7]

DETECTION OF THE PATIENT'S EEG PARAMETERS
FOR THE BRAIN VISUAL CORTEX ACTIVATION CALCULATION

[OK]  [KEEP THE PREVIOUSLY USED PARAMETERS]

IT IS RECOMMENDED TO USE THIS STEP OF THE THERAPEUTIC
DURING EVERY SESSION IN ORDER TO INCREASE THE EFFICIENCY
OF THE EEG ANALYSIS. HOWEVER, IT IS POSSIBLE TO USE THE EEG
PARAMETERS CALCULATED FOR THE PREVIOUS SESSION.

OPTICAL CORRECTION
VOD [SPH +9.0D CYL+1.5D AX 015]
VOS [SPH +9.5D CYL+2.5D AX 160]

POSITION THE PATIENT IN FRONT OF THE TV SCREEN.
INFORM THE PATIENT THAT HE/SHE SHOULD VIEW
A COUPLE OF DOZEN OF DIFFERENT PICTURES.
FOR THE INITIATION OF A PROCEDURE PRESS "OK"

[OK]
[CANCEL]

Fig. 14C

BEFORE STARTING THE TREATMENT, PLEASE, VERIFY PATIENT'S NAME,
OPTICAL CORRECTION AND OTHER INFORMATION

PATIENT [RICHARD LEONARD] SESSION [7] FROM [20]
OPTICAL CORRECTION            MODE
[PAUSE] VOD [SPH +9.0D CYL+1.5D AX 015]   [RELAXATION]
        VOS [SPH +9.5D CYL+2.5D AX 160]   VIEWING
                                          [LEFT EYE]

EEG
A

[10 MINUTES]
[LEFT 04 : 06]

EOG
EMG

[OK]
[CANCEL]

Fig. 14D

VISUAL TRAINING SYSTEM AND APPARATUS FOR VISION CORRECTION, ESPECIALLY FOR VARIOUS FORMS OF STRABISMUS ("CROSSED" EYES)

This application claims the benefit of U.S. Provisional Application No. 60/055,859, filed on Aug. 15, 1997.

BACKGROUND

1. Field of Invention

This invention relates to vision correction methods and an apparatus which uses a biofeedback approach and brain wave evaluation while simultaneously monitoring eye movement, evaluating the eye-movement function for interference, and establishing a trend.

2. Description of Prior Art

Amblyopia—the loss of vision due to "disuse" of the eye(s)—is the most common cause of visual loss in American children (Krueger and Elderer, 1984). It is caused by inadequate visual stimulation of the brain during the critical period of visual development. The most common cause of amblyopia is strabismus—misaligned or "crossed" eyes. Primary strabismus leads to amblyopia through the neural mechanism of suppression, because the brain ignores images coming from the crossed eye. About one-third of all persons with strabismus are diagnosed for amblyopia (Elder, 1994). Strabismus and amblyopia affect about 5% of the population (Nelson, 1984). Sensory strabismus results from any primary cause of visual loss. If vision is poor in one or both eyes, fusion (the brain's ability to use both eyes together and thereby attain and maintain depth perception) cannot occur and ocular alignment is lost due to a partial loss of brain control. The treatment of strabismus is aimed at: 1) eliminating amblyopia; and 2) realigning the eyes to restore binocular perception.

In ophthalmology both surgical and non-surgical (or functional) methods are applied for treating strabismus. The surgical methods demonstrate fast and radical results, but there are many contra-indications for surgery such as high occurrence of complications and, most of all, possibility of reoccurrence of symptoms of strabismus after surgery. Thus, there is no reasonable basis for the preference of surgical methods.

There are two groups of non-surgical methods used for treatment of "crossed" eyes: occlusion methods and those using a biofeedback procedure. Until recently the most effective non-surgical method for treating of strabismus was occlusion. This method is based on the occlusion of the dominant eye by patching and thereby forcing the crossed eye to perform the visual function. The origination of this procedure goes back to the 18$^{th}$ century (Saint-Yves, 1722. Cited in Hischberg, 1984; Buffon, 1743. Cited in Wilkinson, 1943).

The occlusion therapy alone (Elder, 1994) or in combination with pharmacological treatment (Kubota and Usui, 1993) has an efficiency in the range of 40–70% and is not entirely successful (Flynn and Cassady, 1978). For most effective results, the occlusion treatment must be made during the first 6–7 years of the person's life. As a result, this generally limits the effective use of these methods to young children. The treatment also should continue for up to 2 years. The duration of treatment is deemed as a burden and an inconvenience. There is also very high recurrence of strabismus after treatment is discontinued. In addition, because these children and young adults are in their formative years, they continue to participate in school and engage in other normal social activities. As a result of their reduced visual function, however, such participation can lead to distress and a decision to discontinue further treatment. There are also cosmetic concerns and concerns about allergies to certain types of patches used for occluding vision.

Another treatment method is biofeedback therapy. This is a technique which is based on conditioning principles and has been used in a variety of applications. The technique provides a person with immediate information from the biological process which normally is beyond his conscious awareness, thus facilitating voluntary regulation of these same functions. The methods for vision correction based on a biofeedback procedure can be divided into two categories. The first method is targeted on the improvement of visual acuity of the eye with a misaligned optical axis. The methods falling in the second category use autotraining to develop endogenic reflectory mechanism in order to reduce the degree of optical axis misalignment in the crossed eye.

Both methods are based on theoretical assumptions similar to those in the occlusion therapy. It is assumed that the occlusion of the dominant eye during the treatment procedure inclines the eye with reduced visual function to participate actively in visual perception. The improvement of visual acuity in the treated eye, the theory continues, leads to gradual recovery of the binocularity (and visa versa for the second method) and the increased control over the oculomotor muscles by the central nervous system. This results in restoration of the optical axis and the cure of strabismus.

Among applications subscribing to the first method is the Russian Federation Patent 2070011 to Tumanyan (issued Dec. 10, 1996) disclosing the method of visual function correction specifying amblyopia treatment. This invention suggests the approach for treatment of amblyopia by the restoration of vision acuity. This method uses detection of the person's electroencephalogram (EEG) with computer analysis performed after amplification of the signal. The distinctive feature of this method is the use of spontaneous fluctuations of EEG alpha-waves as a factor controlling the switch of a movie being viewing by a person. The spontaneous intensification of EEG waves is considered as a sign of the relaxed state of the brain structures connected to visual functions. In contrast, the decrease of the intensity of EEG alpha-waves indicates visual cortex activation. In presence of myopia (nearsightedness) and a diagnosis of the anisomyopic amblyopia the spontaneous occurrence of brain relaxation (correspondent to the increase of the intensity of EEG alpha-waves) is considered as a positive trend and is encouraged by an opportunity to watch the movie. In situation involving hyperopia (far-sightedness) and a diagnosis of the anisohypermetropic amblyopia or the strabismic amblyopia, the activation state of the brain (correspondent to the decrease of the intensity of EEG alpha-waves) is supported. The described biofeedback procedure is repeated daily for 20–30 minutes during 20 days (this is referred to as one course). The results of the treatment with this technique are discussed below.

U.S. Pat. No. 4,896,959 (issued Jan. 30, 1990) to O'Brien discloses a visual acuity unit for treatment of amblyopia through the use of a solitary visual target maintained at a level of minimal discernible size. This method is limited only to use by persons with a lack of acuity which is not of a refractive or transparent nature. Young persons would have difficulties using this apparatus because of its complicated nature and the associated tasks to be performed. Also, it would have the same difficulties associated with persons having amblyopia and severe degrees of strabismus. The same is true for other methods which employ only a training of the acuity of vision without a restoration of the alignment of the optical axis.

An example of the second method used for biofeedback therapy was described in (Goldrich, 1982). In this method persons were trained to achieve and sustain alignment of the optical axis by receiving an audio-feedback signal. The eye position was monitored with an instrument using a spectacle frame holder with a pulse-rated infrared (IR) emitter diode and two rated IR photo cell detectors in front of each eye. Detection of lateral eye movement was limited to about 0.5 degree. The changes in ocular vergence movements were recorded, amplified and outputted to the voltage-regulated audio oscillator. An audible tone of variable pitch could be heard as the eyes behind the IR detectors assumed different vergence positions. The more extreme the vergence position the higher the pitch. Different optical charts (e.g., Snellen letters and other reading material) have been used as visual stimuli. Therapy was administered in weekly hour-long sessions with frequent brief rest periods. The results are discussed below.

A similar approach is disclosed in U.S. Pat. Nos. 4,533,221 and 4,660,945 to Trachtman. The method to train a person to improve visual focusing ability has been suggested. Analogously to the method described by Goldrich, the refraction of the eye was measured and used to produce a tone to which a person may be trained to respond by driving up the pitch. The eye refraction detection during the therapeutic session requires a long-time fixation of the head which renders this kind of treatment almost impossible for children. Moreover, the refraction of the eye does not describe synchronizing eye movement of both eyes which is important, especially for treatment of persons with strabismus. Also, audio-tone used for a biofeedback signal is not the optimal choice for young children.

U.S. Pat. No. 5,374,193 (issued Dec. 20, 1994) to Trachtman discloses the method and apparatus for training to remain in alpha-state (then the brain emits alpha-waves) using the EEG for the brain state evaluation and using EMG for muscle tension detection. Improved methods of reflected-back radiation from the eye detection incorporating a two-dimensional CCD matrix has been used. The EMG has been used for relaxation training. Such training to remain in the alpha-state may be useful for vision improvement in adults, but much less effective in young persons due to their having poorly expressed alpha-waves. The application of this method requires the long-time fixation of the head to a holder. This is physically inconvenient for a person, particularly one of tender years.

Russian Federation patent 2061508 to Mikhailenok (issued Jun. 10, 1996) based on the USSR Inventor's Certificate 1688867 (Jul. 8, 1991) discloses the method of functional correction of neuro-muscular dysfunction (e.g., poor posture, scoliosis) and spasm of accommodation in ophthalmology. In this method the person's bioelectric activity of the brain (EEG) or the muscle (EMG) is detected. Then the signal is analyzed with a computer algorithm and the decision to let the person play a video-game is made based on the results of the analysis. The distinction of this method is in the use of a video game as an attractive goal for children. Previous methods generally used audio signals or other means which do not interest or stimulate children stimuli thereby resulting in a lower efficiency rate of the treatment.

U.S. Pat. No. 5,363,154 (issued Nov. 8, 1994) to Galanter discloses computer based vision training method and apparatus.

None of these devices and methods has incorporated the unique features of the present invention. Our invention incorporates a new method and an apparatus to restore visual function in the misaligned eye by controlling movements of the eyes in conditions close to the natural process of visual perception (e.g., watching a movie or playing a game) with the simultaneous encouragement to increase a visual acuity.

The disadvantages of prior applications include:

a. Surgical methods, although fast and radical, have many contra-indications, lead to complications in post-surgery period, and do not eliminate a possibility of a recurrence of strabismus.

b. Occlusion therapy is not quite effective and also has a high recurrence rate. It must be started at very early age and continue for up to 2 years leading to distress at school and precluding the child's participation in many activities because of his greatly reduced visual functions. There are also cosmetic concerns and possible allergic reactions.

c. Known methods of biofeedback therapy based on the restoration of visual acuity of the eye with a misaligned optical axis are only about 50% effective. This is due in part to inadequate choices of the EEG components for the brain state evaluation. The brain alpha-waves used in these techniques are poorly expressed in young children with low visual function and therefore provide no opportunity for efficient and effective analysis. This in turn limits the application of methods employing analysis of brain alpha-waves (R.F. Patent 2070011 to Tumanyan; U.S. Pat. No. 5,374,193 to Trachtman).

For example, using the method described by Tumanyan (Russian Federation Patent 2070011) a better efficiency of the treatment has been observed in persons with anisohypermetropic and strabismic amblyopia (about 70%) whereas for persons with anisomyopic amblyopia the efficiency was about 45%. The remission after 1–2 courses of the treatment was considered a successful treatment. Taking into account the frequencies of occurrence of different forms of amblyopia, total efficiency was about 55% (Tumanyan et al, 1993). A rather low efficiency of this method for treating anisomyopic amblyopia corresponds to how EEG signals are expressed and analyzed. The EEG alpha-waves used for the brain state evaluation in this therapy are poorly expressed in young children (3–5 years old). Children suffering from amblyopia exhibit even weaker alpha-waves than their healthy counterparts, which makes analysis of the EEG alpha-waves almost impossible. Older persons generally have better pronounced alpha-waves, but treatment in this group is less efficient. Wrong position of the eye with misaligned optical axis is already fixed in older persons and their CNS is unable to sufficiently control the visual function of this eye. In addition, the oculomotor function of the eye is not analyzed in this method.

Second, this kind of therapy has a low effect on persons with severe degrees of misalignment of the optical axis (severe strabismus). This can be explained by the inability of the person's CNS to control visual function in the "crossed" eye without normalizing its optical axis.

Among the methods discussed above, those described by Trachtman (U.S. Pat. Nos. 4,533,221, U.S. Pat. No. 4,660,945 and U.S. Pat. No. 5,374,193) provide a detection of the refraction of the eye to evaluate movements of the eye. But this method lacks the complete description of the eyes' movement function (e.g. it is impossible to detect synchronization of movement because the refraction from only one eye is detected). Also, the use of audio-signal for a biofeedback connection is not an optimal choice.

The biofeedback procedure for developing a reflex mechanism in order to reduce the degree of optical axis misalignment was unsuccessful for persons with significant loss of vision and/or severe degrees of misalignment. A low visual acuity results in the failure of the CNS to control the amblyopic eye's visual function including the alignment of its optical axis. Therefore, without improvement of visual acuity, the misaligned eye is unable to restore the connection between the CNS and the eye which is necessary to achieve realignment of the optical axis. Also, the audio-feedback signal used in this therapy is not interesting for children. This makes it difficult to obtain their full participation in the procedure. In addition, as previously described, the manner in which eyes movements are detected in this technique is not very comfortable for a person.

For example, the training described in (Goldrich, 1992) was about 80% efficient for persons with mild degrees of divergence of the eyes. These persons usually have sufficient visual acuity to be able to control eye movements. However, for persons with significant loss of vision and strabismic amblyopia a positive result was achieved only in about 20% of cases. Moreover, these results were unstable. The failure to cure persons with low vision by this therapy is explained by an absence of preliminary improvement of visual acuity in the misaligned eye. It is known that low visual acuity in the amblyopic eye is connected to the failure of the CNS to control this eye's visual perception including the alignment of its optical axis. Therefore, without attempts to improve the misaligned eye's visual acuity and restore CNS control of visual function these methods are very unlikely to realign the optical axis. Thus, persons with severe strabismus are not helped by this kind of therapy. Besides the neurophysiological explanation, it is reasonable to consider alternate methods to stimulate the person in his attempts to maintain the eyes in correct alignment. To gaze on a motionless point is not a physiologically correct task for an adult and it is especially difficult for children. Also, for very young children, it is difficult to obtain full participation because of their lack of interest.

Accordingly, several objects and advantages of the present invention are:

a. to provide an easy-to-use apparatus for training for simultaneous improvement of visual acuity and realignment of the optical axis therefore taking into account needs of persons with different forms of strabismus and amblyopia;
  b. to avoid different side effects caused by invasive methods and permanent patching of the defect eye;
  c. to describe visual function of the defect eye by dynamic spectral analysis (Fourie analysis) of alpha-, beta-, and theta-waves detected in the person EEG while avoiding artifacts caused by the age of the person and to improve the quality of description of the brain visual activation function compared to methods limited to the use of only the alpha-component of brain waves;
  d. to take into consideration the individual characteristics of the person by analysis of the person eye reaction to an unstructured image and to a structured image of the same brightness and by calculating individual coefficients for visual function analysis;
  e. to evaluate the synchronism (including time, direction and amplitude) of the eyes' movements by detection and analysis of the person's electrooculogram (EOG) of both eyes and providing a novel way to characterize eyes' movement function and avoid long-time fixation of the head and other inconveniences for the person; and
  f. to use the electromyogram picked up from m. orbicularis oculi in order to account for any interferences caused by blinking.

Further objects and advantages of the present invention include providing a system for vision correction which can be used easily by medical personnel and be convenient for persons as will become apparent from a consideration of the drawings and ensuing description.

BRIEF DESCRIPTION OF THE DRAWINGS

The invention will be better understood with reference to the following illustrative and not limited drawings, in which:

FIGS. 7A to 7E illustrate the definition of the eyes' movements function $\Delta$;

FIGS. 8A to 8F illustrate the EOGs analysis, calculation of eyes' movements function $\Delta$ and determination of a trend of this function;

FIGS. 14A to 14D show computer screen on different stages of a procedure;

SUMMARY

The present invention relates to a vision correction apparatus, and more particularly, a vision correction apparatus for correcting various forms of strabismus. The apparatus comprises a viewing means for viewing images, a dynamic stimulus device to be engaged or disengaged depending on control signals generated from the apparatus, a measuring means for observing and measuring viewing activity of the user, data storage means for storing data measured by the measuring means, and control means for assessing stored data and, in relation to an assessment made of the stored data, for generating and transmitting a control signal to engage or disengage the dynamic stimulus device. The measuring means further measures alpha, beta, and theta brain waves after viewing a structured and an unstructured image for a pre-determined period of time, observes and measures electrooculogram (EOG) patterns of each eye, and observes and measures interfering muscular movement but use of an electromyogram (EMG) after which the data obtained from the measurements is assessed by the control means to establish individualized normalizing coefficients and values, to establish brain visual activation function and value, to establish absolute differences between EOG patterns of the eyes, to account for interfering muscular movement not associated with EOG patterns, and to establish a trend which, if supportive of vision correction, engages the dynamic stimulus device and, if not supportive of vision correction, disengages the dynamic stimulus device thereby encouraging a user to self-correct by repeating activity which engages the dynamic stimulus device.

DETAILED DESCRIPTION OF THE DRAWINGS

The preferred embodiment of the vision correction system will be discussed next. Due to a complexity of the signal analysis performed by the vision correction apparatus, the new process to analyze a brain visual activation function (referred to as A for equation purposes and by the acronym BVAF) will be discussed first with its biofeedback principle. This discussion will be followed by an explanation of monitoring, determination and analysis of signals used for the improved eye-movement function description. Thereafter, the complex analysis of all signals during the therapeutic mode will be explained. After this explanation has been accomplished, the connection between all parts of the apparatus will be described. This description will be then followed by a short illustration of operation during the vision correction session utilizing this apparatus.

Figure 1:
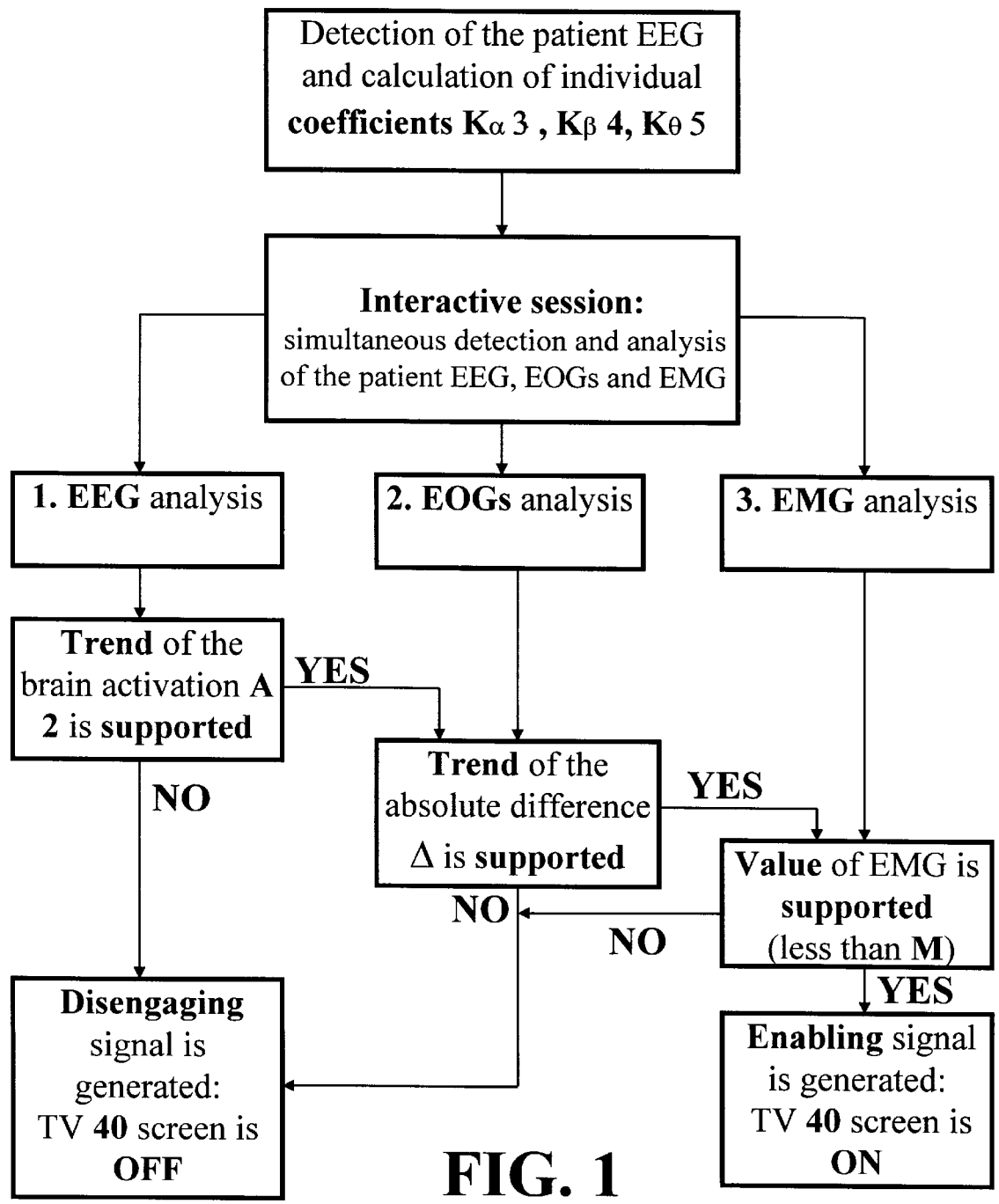
FIG. 1 shows the flowchart of the therapeutic procedure with a biofeedback signal generation (general structure)—this is a block diagram of a preferred embodiment in accordance with the present invention.

The flowchart shown on FIG. 1 illustrates, in general, the operation of the apparatus as used to conduct a session of vision correction for a person 1. The first step in this procedure is for the apparatus to establish individual coefficients referred as K$\alpha$,3 (individual normalizing coefficient for alpha-waves), K$\beta$, 4 (individual normalizing coefficient for beta-waves) and K$\theta$, 5 (individual normalizing coefficient for theta-waves) of a person's brain visual activation function (BVAF) A, 2 which takes into consideration all parts of human brain waves emitted in an awake state.

Figure 2:
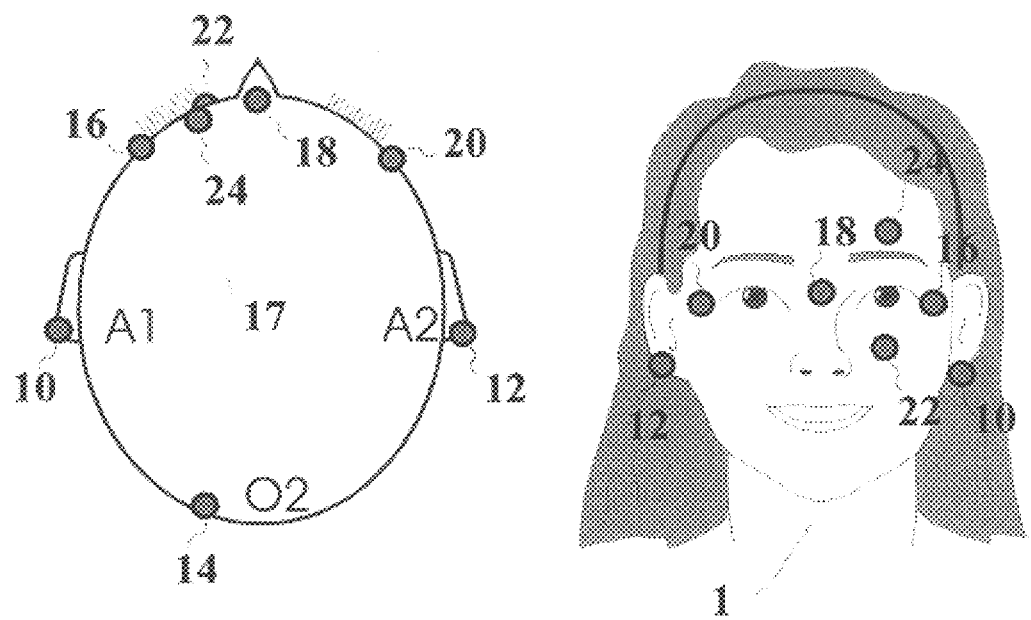
FIG. 2 is a schematic sketch of a person's head and the electrodes positioned for the recording of the person's EEG (electroencephalogram), EOG (electrooculogram) of both eyes and EMG (electromyogram)

A person 1 is comfortably positioned, for example, in front of a display device or other viewing means such as, by way of example only and not by way of limitation, a TV 40 or other device suited for the intended purpose and instructed to relax. During this step both eyes are open and the optimal optical correction (by glasses, lenses or other fashion) is provided. As illustrated in FIG. 2, electrodes 10, 12, 14 are positioned on a person's head 17 by a scheme referred to as "10–20", which is known to a person skilled in the art. Basically what this scheme entails in administering an EEG is the use of three electrodes. Two are for auriculas (referred to in the Figure as A1 and A2) and one for occipitalis (referred to in the Figure as O2). Electrode 10 (A1-left auriculas electrode) is positioned on the person's left ear, electrode 12 (A2-right auriculas electrode) is positioned on the patient's right ear, and electrode 14 (O2-occipitalis electrode) is positioned on the back of the person's head.

Figures 4A, 4B, 4C, 4D:
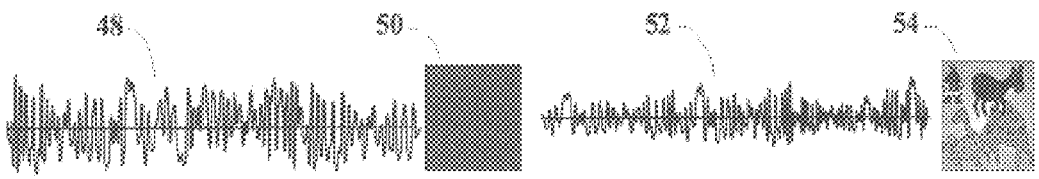
FIGS. 4A to 4D illustrate the calculation of the person individual normalizing coefficient for alpha-waves $K\alpha$, individual normalizing coefficient for beta-waves $K\beta$ and individual normalizing coefficient for theta-waves $K\theta$.

Other electrodes are positioned as follows: one on the person's nose between the eyes 18, one on the outside of the person's right eye socket 20, one positioned below one of the person's eyes 22, and one above one of the person's eyes 24. Electrodes 10, 12, 14 pick up an electroencephalogram (EEG) 21 from the person's brain. The activity of the person's brain is recorded in two modes. The first mode is represented in FIG. 4A. This is where an EEG taken during an unstructured image viewing 48 is recorded or stored as a person 1 looks at a static unstructured image (blur picture) 50 for 1 minute. The second mode is represented in FIG. 4B. An EEG taken during a structured image viewing 52 is recorded or stored as the person looks at a structured image (picture) 54 for 1 minute. Both images have the same color representation, density and brightness. Both modes are repeated 11 times for 11 pairs of images.

Figure 5:
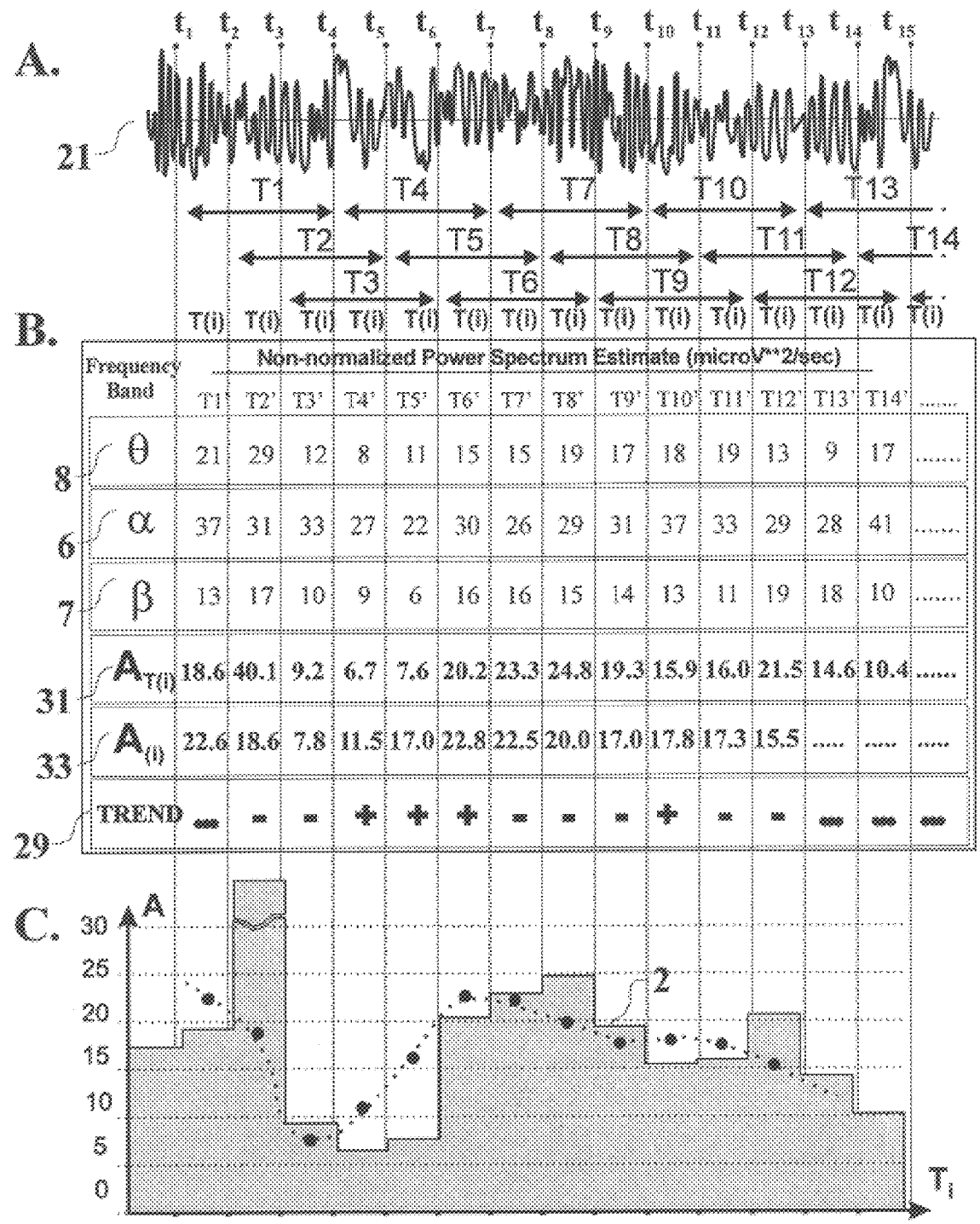
FIGS. 5A to 5C illustrate the calculation of the brain visual activation function A and detection of a trend of this function.
Figure 6A:
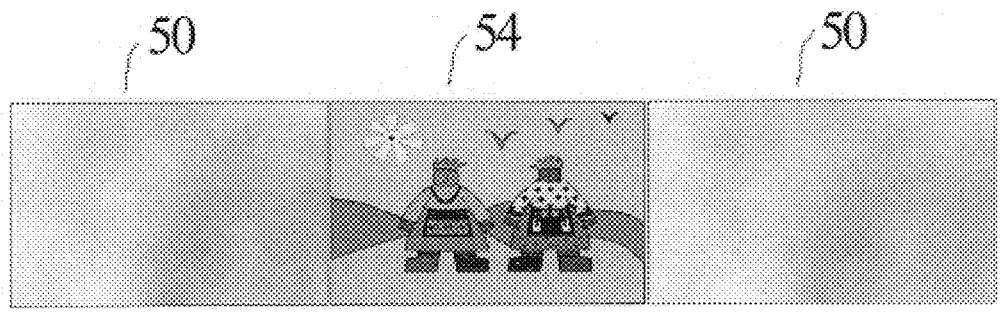
FIGS. 6A to 6C illustrate the brain visual cortex activation during a picture viewing by a normal eye and by an amblyopic eye.
Figure 6B:
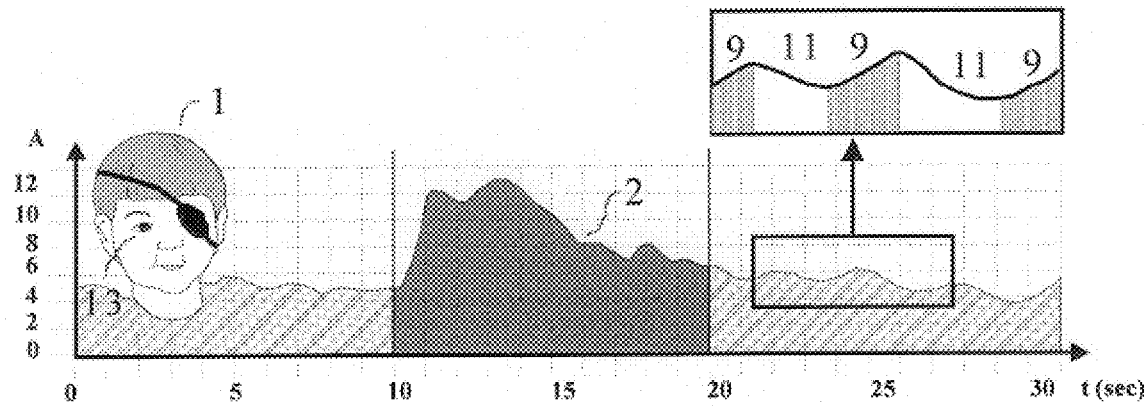
Figure 6C:
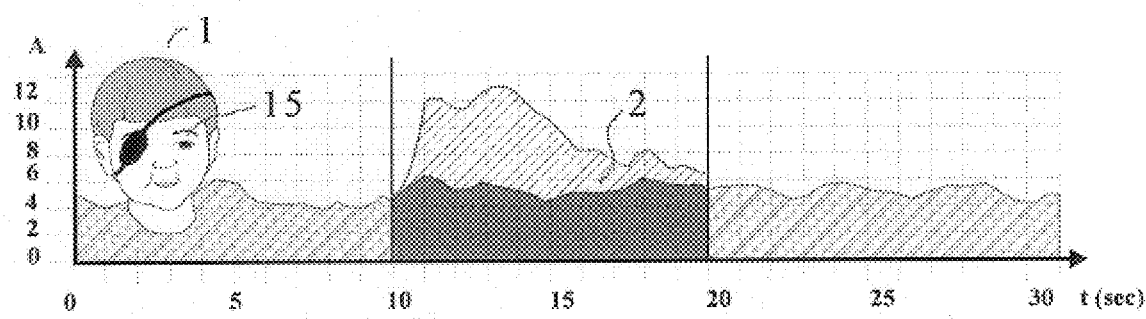

The present invention classifies the brain wave outputs from electrodes 10, 12 and 14 between brain alpha-waves 6 (8–13 Hz, a measure of alertness), brain beta-waves 7 (>14 Hz, the normal waking sate), brain delta-waves (0.5–3 Hz, the sleep state), and brain theta-waves 8 (4–7 Hz, the creative state). This classification process is referred to a band-pass filtering and, in the preferred embodiment, is performed by a source code 70 in a computer 36. It must be understood, however, that the detection of the person's EEG and its concomitant classification of brainwaves (i.e., the band-pass filtering) can be done by any other suitable mechanisms and is not limited to computer-assisted classification. It is known that intensification of cerebral neurophysiological processes in a human brain results in changes of EEG parameters: less pronounced alpha-waves (8–13 Hz), increased fluctuations in beta-waves (14–25 Hz), and, usually in children, increased theta-waves (4–7 Hz). All these changes are specific for each person. The apparatus also provides for establishing individual characteristics for every person, which fosters an opportunity to improve upon previously described techniques. Normalized power spectrum estimates for each component of brain waves (alpha 6, beta 7, and theta 8 as illustrated in FIG. 5) recorded during both modes of image viewing are determined using the dynamic spectral analysis (Fourie analysis), a mechanism known to a person skilled in the art. Thereafter the apparatus establishes what is referred to as individual normalizing coefficients (referred to as INC or by the symbol 'K' hereafter) K$\alpha$ 3, K$\beta$ 4, and K$\theta$ 5. These INC's are established as a ratio of corresponding normalized power spectrum estimates, which basically are percentages, detected during a viewing of structured image 54 to the corresponding ones detected during a viewing of unstructured image 50. Equations 1, 2, and 3, below detail how this is accomplished.

These individual normalizing coefficients (INC's) are unique to each specific person and reflect the difference between an activated visual cortex and a resting visual cortex of the brain taking into consideration all parts of brain activity during an awake state. An example of the calculations which utilize the equations 1, 2, and 3 for a hypothetical person is shown in FIG. 4C. The normalized power spectrum estimate for beta-waves for this person is 13 for unstructured viewing and 18 for structured viewing, alpha-waves for this person is 48 for unstructured viewing and 33 for structured viewing, and theta-waves for this person is 39 for unstructured viewing and 49 for structured viewing. The beta-INC (or K$\beta$) therefore is 1.38, the alpha-INC (or K$\alpha$) is 0.69, and the theta-INC (or K$\theta$) is 1.26

$$K_\beta = \frac{\beta_{\text{structured image}}}{\beta_{\text{non-structured image}}} \quad \text{(Equation 1)}$$

$$K_\alpha = \frac{\alpha_{\text{structured image}}}{\alpha_{\text{non-structured image}}} \quad \text{(Equation 2)}$$

$$K_\theta = \frac{\theta_{\text{structured image}}}{\theta_{\text{non-structured image}}} \quad \text{(Equation 3)}$$

In contrast to previously described methods which employ only EEG alpha-waves for the brain state analysis, in the present invention the control over activation and relaxation of the brain's visual system is carried out by the analysis of a complex parameter referred to herein as a brain visual activation function 2 and designation by a letter A or the acronym BVAF. This parameter is a dynamic variance of brain alpha-, beta-, and tetha-waves. The apparatus establishes the brain visual activation function (A) by employing Equation 4 below (an example of this equation using the values derived from FIG. 4C is illustrated in FIG. 4D).

$$A = \frac{(K_\theta \times \theta) \times (K_\beta \times \beta)}{(K_\alpha \times \alpha)} \quad \text{(Equation 4)}$$

Reference to FIGS. 5A–5C is important for a better understanding of the internal operation of the apparatus. FIG. 5A illustrates a graphic representation 21 of our hypothetical person's EEG waves. The apparatus establishes a window (or windowing) for a dynamic spectrum analysis (the Fourie analysis) of the respective observed brain waves. The Fourie analysis is well known to a person skilled in the art and is shown in FIG. 5A. Vertical lines on the chart correspond to time intervals or time windows (referred to as T(i) for equation purposes and represented by that symbol in FIG. 5A and by symbol T#' in FIG. 5B), each time window is equal to ⅓ second (333 ms). Time points are illustrated by the symbol t# and are identified as specific time points t1, t2, t3, on FIG. 5A For example, the column in FIG. 5A represented by time points t1 and t2 correspond to time interval T1' in FIG. 5B. For the present invention, we have selected one second to the length of a time period for a dynamic spectrum analysis of the person's EEG. A time period is designed by character T# as illustrated in FIG. 5A by horizontal lines spanning three intervals. Time period T1 begins at time point t1 and continues up to time point t4 as shown in FIG. 5A.

To avoid any time-smoothing effects which may occur when T# >>one second; as well as to avoid component dominance which may occur when T# <<one second. Each time period T1, T2, T3, etc., is equal to one second, and the beginning of each succeeding time period has a time lag equal to ⅓ of a second (represented hereafter as T(i+1)) to the previous time interval T(i) and an overlap of ⅔ of a second therein. For example, time period T1 of FIG. 5A commences at time point t1 and continues through time point t4. Time period T2 commences at time point t2, ⅓ of a second after time period T1 began (or at T(i+1) overlapping time period T1 by ⅔ of a second), and continues through time point t5; time period T3 commences at time point t3, ⅓ of a second after time period T2 began and overlaps time period T2 by ⅔ of a second, and continues through time point t6; and so on. Consequently, each window used in our analysis is a time interval (T(i) or T#') and begins with a time period (T#) at a time point (t#), runs for one second (containing three T(i)s or T#'s therein), and is overlapped with the beginning of the next time period or time window by ⅔ of a second or T(i+1).

The highest (Nyquest) frequency in the analyzed signal determines a necessary sampling rate in analog-to-digital conversion. This is a process which is well known in the art. Under this process in our case, it means that at least five measurements of the function value during one time period (T# or one second) corresponding to highest frequency in the signal should be made to provide a good quality of analysis. Since the maximum frequency for an EEG is about 30 Hz, 5 measurements must be taken during each single frequency cycle (the duration for each cycle being about 33 milliseconds). One EEG measurement consisting of about 30 Hz, therefore, must be taken about every 6.6 milliseconds. Five times of the EEG maximum frequency of 30 Hz (or five measurements thereof every 6.6 milliseconds within T#) is equal to about to 167 Hz (i.e., the duration of one cycle [33 ms] in relation to one second [1000 ms] yielding 167 Hz). Thus, in order to provide a frequency of data recording equal to 167 Hz, every second (the respective window) 167 new EEG samples are recorded and analyzed.

The windowing conducted in the present invention (number of T(i) or T#' within one T# and measurements thereof) can be done more often than 3 times per second, but this does not increase the accuracy of the biofeedback signal determination, because fluctuations of the brain visual activation finction A are low-frequency ones (about 1 Hz, which corresponds to 1 second). It is therefore inefficient to provide biofeedback signals more often than the brain can use. Also incorporating more frequent biofeedback increases the cost of the apparatus. The windowing generally shouldn't be done less often. To do so could result in missing and not detecting fluctuations in the brain visual activation function A. A reasonable frequency to analyze a person's EEG 21 and to generate biofeedback signal 72 is not less than 2–4 times per second. A frequency for the biofeedback signal generation in a preferred embodiment is chosen to be 3 times per second, but our apparatus is not limited to this value. It provides a combination of high accuracy and lower cost of signal processing.

Power spectrum estimates (values in each column in FIG. 5B) for each window T(i) or T#' have been determined for all frequency bands (brain alpha-waves 6, brain beta-waves 7, brain theta-waves 8) using a standard technique of dynamic spectrum analysis known to a person skilled in the art. First the observed values or measurements are obtained for each interval T#' for each brain wave. For example, for theta-waves 8, the observed measured value for interval T1' is 21, for alpha-waves 6, the observed value for interval T1' is 37, and for beta-waves 7, the observed value for interval T1' is 13. These observed values are the values for the respective theta, beta, and alpha values used by the apparatus to establish the BVAF value for each specific moment in time; that it, for each time interval. This value is referred to as the BVAFV and in FIG. 5B and for equation examples as $A_{T(i)}$ (represented as reference numeral 31 encompassing the entire horizontal row in FIG. 5B).

For each given window T#', therefore, the apparatus establishes a BVAFV. Equation 5 is employed for that function.

$$A_{T(i)} = \frac{(K_\beta \times \beta(T(i))) \times (K_\theta \times \theta(T(i)))}{K_\alpha \times \alpha(T(i))}, \quad \text{(Equation 5)}$$

The BVAFV values of our hypothetical person are set forth in FIG. 5B and have been established from that person's respective coefficients Kα=0.69, Kθ=1.26, and Kθ=1.38 and respective observed measurements of 37 (alpha), 13 (beta), and 21 (theta).

The BVAFV values 31 [or $A_{T(i)}$] represented in the table in FIG. 5B are discrete values of the continuous function and, for a better final result, should be "smoothed" in order to obtain a continuous dependence. To determine a continuous dependence based on the BVAFV's derived, the apparatus thereafter establishes a running average, referred to as $A_{(i)}$ and set forth in the table at numeral row 33. The running average is established for every three consecutive windows T(i), T(i+1), and T(i+2), or T1', T2', and T3' according to the following equation:

$$A_{(i)} = \frac{A_{T(i)} + A_{T(i+1)} + A_{T(i+2)}}{3} \qquad \text{(Equation 6)}$$

As shown in FIG. 5B an example of calculations for our hypothetical person yields the following values:

$A_{(i)}$ [for time period T1]=(18.6+40.1+9.2 [as taken from intervals T1', T2', and T3', respectively in row 31 of FIG. 5B])/3=22.6 [as illustrated in row 33 of column/interval T1'], $A_{(i)}$ [for time period T2]=(40.1+9.2+6.7 [as taken from intervals T2', T3', and T4', respectively in row 31 of FIG. 5B])/3=18.6 [as illustrated in row 33 of column/interval T2'], $A_{(i)}$ [for time period T3]=(9.2+6.7+7.6 [as taken from intervals T3', T4', and T4', respectively in row 31 of FIG. 5B])/3=7.8 [as illustrated in row 33 of column/interval T3'], etc. for $A_{(i)}$.

These averages for each time period (T#; that is for T1, T2, T3, etc.) are now used to establish a trend 29 of the brain visual activation function. The trend of this function may be positive or negative. A trend is considered "positive" (referenced by character 9 in the various figures), if the next average value [or $A_{(i+1)}$] is greater that the previous average value $A_{(i)}$. The trend is considered "negative" (referenced by character 11 in the various figures) if the next average value [or $A_{(i+1)}$] is less that the previous average value $A_{(i)}$ [or where $A_{(i+1)} < A_{(i)}$]. The examples illustrated in FIG. 5B for the 'trend' row 29 reflect negative trends 11 for intervals T2', T3', T7', T8', T9', T11', and T12'; whereas intervals T4', T5', T6', and T10' reflect position trends 9.

The above is the biofeedback function applied in our apparatus. Its application in our apparatus is as follows (FIG. 1 is a flow chart incorporating the operation of the apparatus, FIGS. 2 through 6 support and provide further reference thereto). Generally, the apparatus is attached to a person. After appropriate set-up and calibration, that person views an image with the defect eye. Data from that viewing is collected, assimilated, and stored. A trend is established. The trend is generally comprised of a series of positive and negative assessments based on the BVAFV averages described above. A specific trend is a triggering event to engage a stimulus device which is adapted to encourage or discourage a certain activity (it is supportive) and its opposite trend is the event to disengage the device (non-supportive). In other words, depending on the defect involved and the activity sought to be encouraged, either a negative trend may be supportive and its opposite trend non-supportive to respectively engage or disengage the stimulus device; or the positive trend may be supportive and a negative trend non-supportive of the stimulus device.

Where a positive trend is the triggering event when using our apparatus, the stimulus device 40 will be engaged at time intervals T3', T4', T5', and T10' (see FIG. 5B). At each of these intervals, the stimulus device will engage (turn on, commence, etc.) permitting the person to engage in the activity associated with the stimulus device. For example, where the stimulus device is a television, the person may view the screen; where the stimulus device is a game, the person may play the game; where the stimulus device involves a movie, the movie continues; and so on. The function of the suggested biofeedback mechanism is to train or acclimate the brain to support the trend associated with the triggering event. The apparatus, therefore, is structured to encourage and positively support the BVAFV's which are corrective in nature to the specific defect involved (such as, but not limited to, myopia, hyperopia, and astigmatism) regardless of other diagnoses (such as, but not limited to, amblyopia, strabismus, nystagmus, glaucoma, or other visual system pathologies).

When the brain visual activation function (BVAF) A is used for biofeedback training it provides a comprehensive evaluation whereas use of the brain alpha-waves alone does not. The BVAF takes into consideration all components of the brain's visual cortex activities. The apparatus of the present invention and the method it employs to comprehensively analyze brain state allows one to take into account individual characteristics of each person. It also incorporates the age-independence, which allows to treat persons with weakly pronounced alpha-waves (specific for young children), thereby overcoming the disadvantages of previous applications.

The present invention also incorporates a new means to describe and analyze the movement of a person's eyes utilizing an electrooculogram (EOG). This apparatus is adapted to train a person to control the movements of his eyes is such a fashion, and by means of biofeedback mechanism as described above, to correct defective or abnormal movements. In this regard, the apparatus has a means to capture and record the respective EOG's of the right eye and the left eye of a person and to establish the absolute difference between the EOG of the left and the right eye. This absolute difference is referred to hereinafter as 'Delta' or by use of this symbol 'Δ'. Reference character 19 has been assigned to this function. The following equation describes the Delta function:

$$\Delta = |EOG_{left} - EOG_{right}| \qquad \text{(Equation 7)}$$

Figure 3:
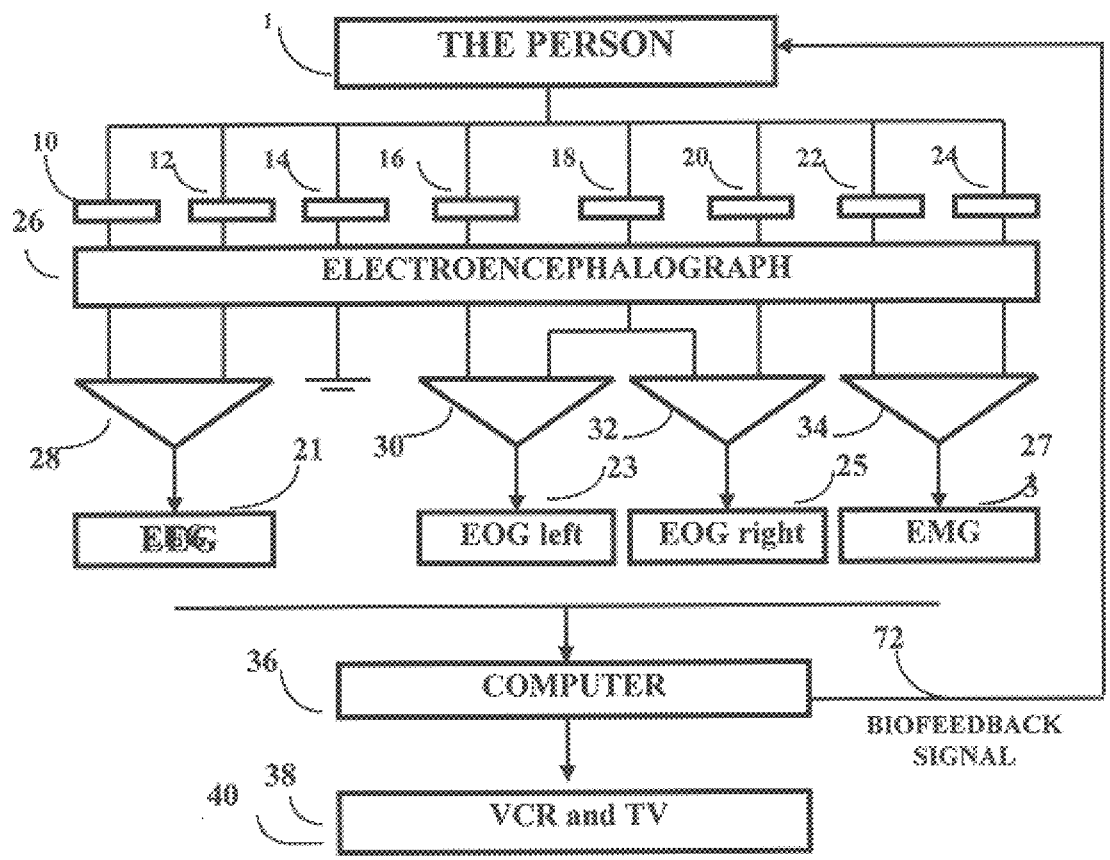
FIG. 3 is a block diagram of the amplification of EEG, EOGs and EMG signals.

FIGS. 1–3 and 7–8 refer to the disclosure which follows. It is known that the eye can be described as an electric dipole. By definition each dipole has a magnitude and a direction. Eye movements in the eye-socket result in electric field fluctuations (in amplitude and/or in direction) and are registerable on the electrooculogram 26 (EOG). The EOG magnitude is equal to the difference between potentials from two electrodes positioned on the outside and on the inside of the same eye-socket. For the left eye this difference, EOG 23, is determined by potentials on electrodes 16 and 18. For the right eye EOG 25 is determined by potentials on electrodes 20 and 18. Positioning of electrodes is shown in FIG. 2. FIGS. 1 and 3 are the flow chart and block diagram of the connection and operation of the present invention.

Figure 7D:
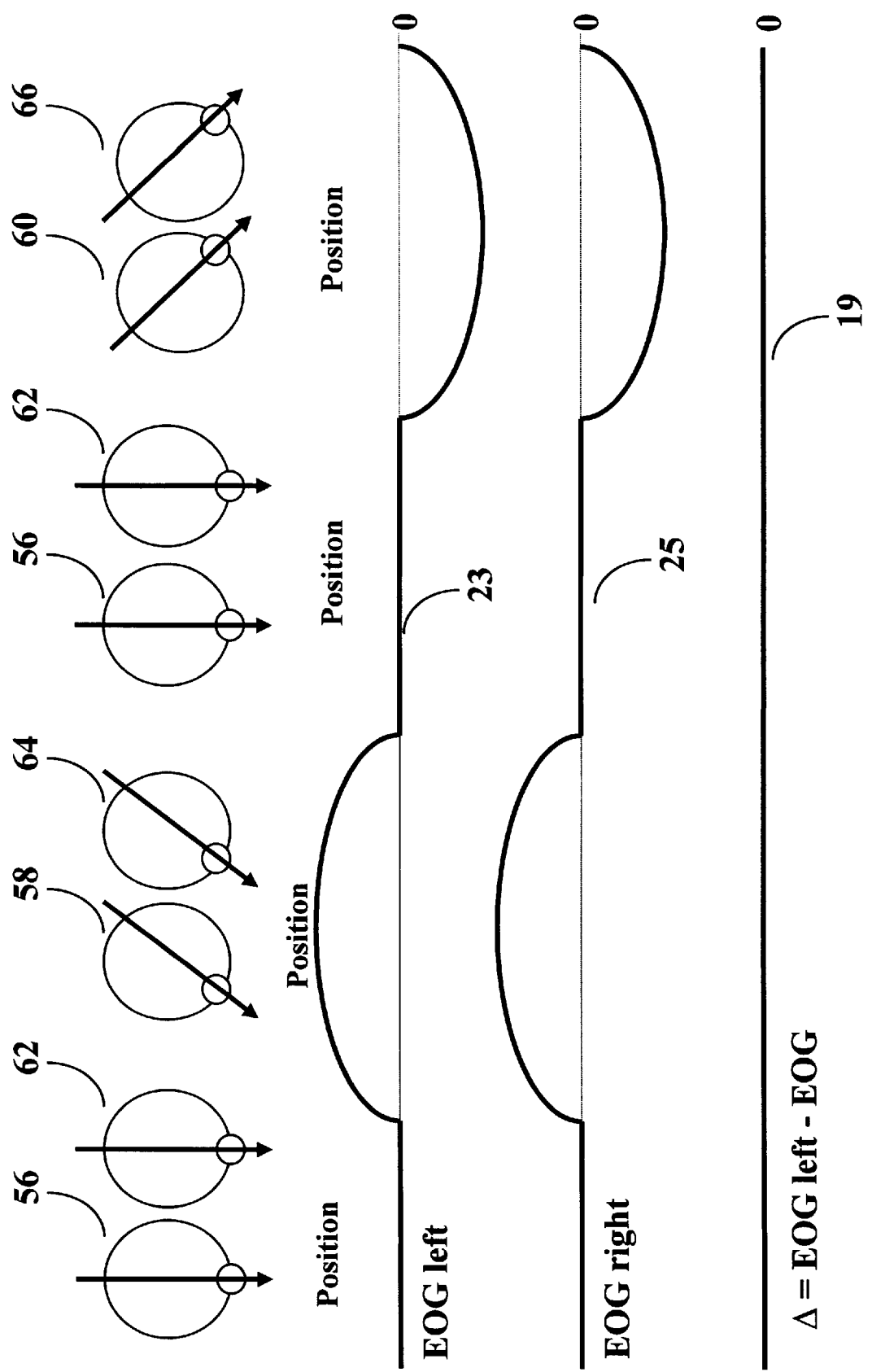

In FIGS. 7A–7E, all eye directions are based on the directional perspective of a person viewing the respective figures. In this regard, FIG. 7A represents a eye looking straight 42. The EOG of this eye is approximately equal to zero because of the identical potentials on both sides of the eye-socket. In FIG. 7B, when an eye looks to the left 44, the EOG of this eye is defined as positive (or greater than zero). In FIG. 7C, when an eye looks to the right 46, the EOG at this moment is defined as negative (or less than zero). When the movement of both eyes is approximately synchronized in time, direction, and amplitude (normal tandem eye-movement function), both eye dipoles will be approximately identical in their magnitude and in their direction. In such a situation, both EOGs will be approximately of the same magnitude. Accordingly, Delta 19, will be approximately equal to zero.

FIG. 7D illustrates normal tandem movement of a person's eyes in the forward position (position 1 56, 62), to the left (position 2 58, 64), forward again (position 3 56, 62), and to the right (position 4 60, 66). In all four positions when both eyes look straight (positions 1 and 3), to the left (position 2), and to the right (position 4) their optical axes are approximately parallel and their movements are approximately synchronized in time and amplitudes resulting in approximately identical EOGs of the left eye 23 and of the right eye 25. Delta (Δ) in this case is approximately equal to zero. FIG. 8A is a graph representative of Delta (Δ) for this individual having normal synchronized eye movement. Delta (Δ) here is very small (it is not equal to zero due to small oscillation movements of normal eyes). If the oculomotor function of the eyes is disturbed by any means, it will result in the asynchronized eye movements.

Figure 7E:
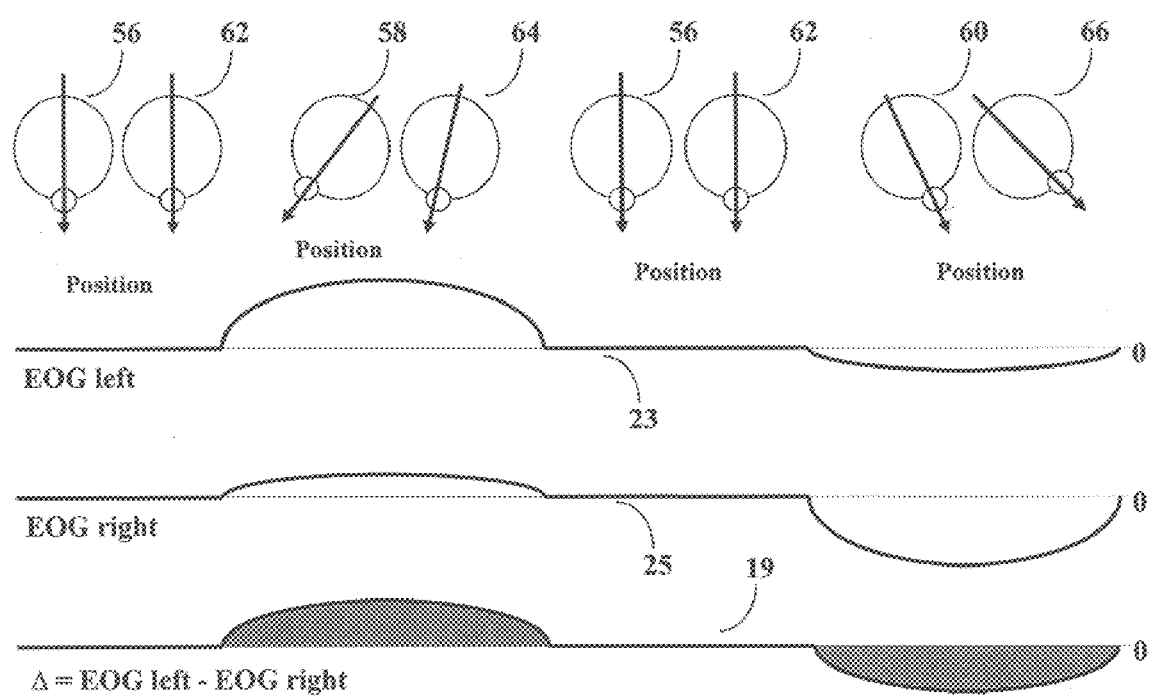

FIG. 7E illustrates eye movement of a person experiencing asynchronization of movement. In the positive position (position 2 58, 64) and the negative position (position 4 60, 66), one eye 58 is offset from the axis of the other eye 64 for position 2 and one eye 66 is offset from the axis of the other eye 60 for position 4. The difference between the left EOG 23 and the right EOG 25 are shown in FIG. 7E below their respective positions. The graphic representation of Delta (Δ) for this person is illustrated in FIG. 8B. As can be seen, the measured differences in movement, Delta (Δ), here is greater than that for a person experiencing approximately synchronous movement as illustrated in FIG. 8A.

The eyes generally experience small oscillations. These oscillations, though normal deviations, may skew the results and operation of the apparatus. A means to factor in normal deviations should be incorporated in any treatment regimen and into the apparatus. One means of establishing a factoring value for normal deviations is to observe and record eye movement and normal deviation of a suitable number of healthy people for a period of time. Any number from 20 to 50 people generally will suffice; any period of time from 5 minutes to 20 minutes generally will suffice. A threshold value, represented by the letter and numeral V, 43 has been established and introduced in this example to distinguish normal and pathological differences for Delta (Δ). This value V was defined as equal to two standard deviations of maximum differences for healthy people EOGs, or 187 microV. With the normal deviation factored into the apparatus, all eye movements exceeding that value (Δ=V= 187 microV) are considered to be abnormal eye-movement.

The value of Delta (Δ) is an adequate physiological parameter to evaluate a person's eye-moving function while viewing a distant object because such a viewing is the most common and natural form of human visual perception. Each parameter of Delta (Δ), 19 (time-synchronization, direction of movement, and amplitude of movement) can be extracted and processed separately. However, this does not make a biofeedback signal more effective.

The analysis of oculomotor function during the biofeedback function of our apparatus is shown in FIGS. 8C–8F. The value of the left EOG 23 (represented in FIG. 8C) is subtracted from the value of right EOG 25 (represented in FIG. 8D). The absolute difference derived therefrom is Delta (Δ). Delta is processed by dynamic spectrum analysis as was described earlier for EEG processing and is represented by FIG. 8E). That is, the highest frequency (Nyquest frequency) of an analyzed signal determines a sampling frequency of AD (analog-to-digital) conversion. Five measurements generally should be taken. The maximum frequency for an EOG is about 10 Hz. One cycle is equal to about 100 ms. At least five measurements of the function during time interval corresponding to Nyquest frequency (time interval T, 37) should be made to provide a good quality of analysis. One fifth of the EOG maximum frequency (100 ms) is equal to 20 ms. Dividing one second [1000 ms] by 20 ms yields 50 times per second or 50 Hz. Due to the requirements for the EEG signal analysis, 167 new data points are recorded and analyzed every second (time interval T, 37) with a time lag ⅓ of a second. This provides a frequency of AD conversion equal to 167 Hz thereby meeting the requirements for an accurate EOG signal analysis.

The apparatus measures the respective EOGs, compares the EOGs, establishes an absolute difference (Delta), if any, and determines a trend (either positive or negative). A trend here is considered positive if the current Delta parameter is less than the previous Delta parameter. A trend is considered negative if the current Delta parameter is greater than the previous Delta parameter. With the Delta parameter incorporated into our apparatus, alone or in conjunction with the BVAFV averages discussed above, the present invention provides for greater flexibility in treating various eye defects, individually or comprehensively.

Figure 9:
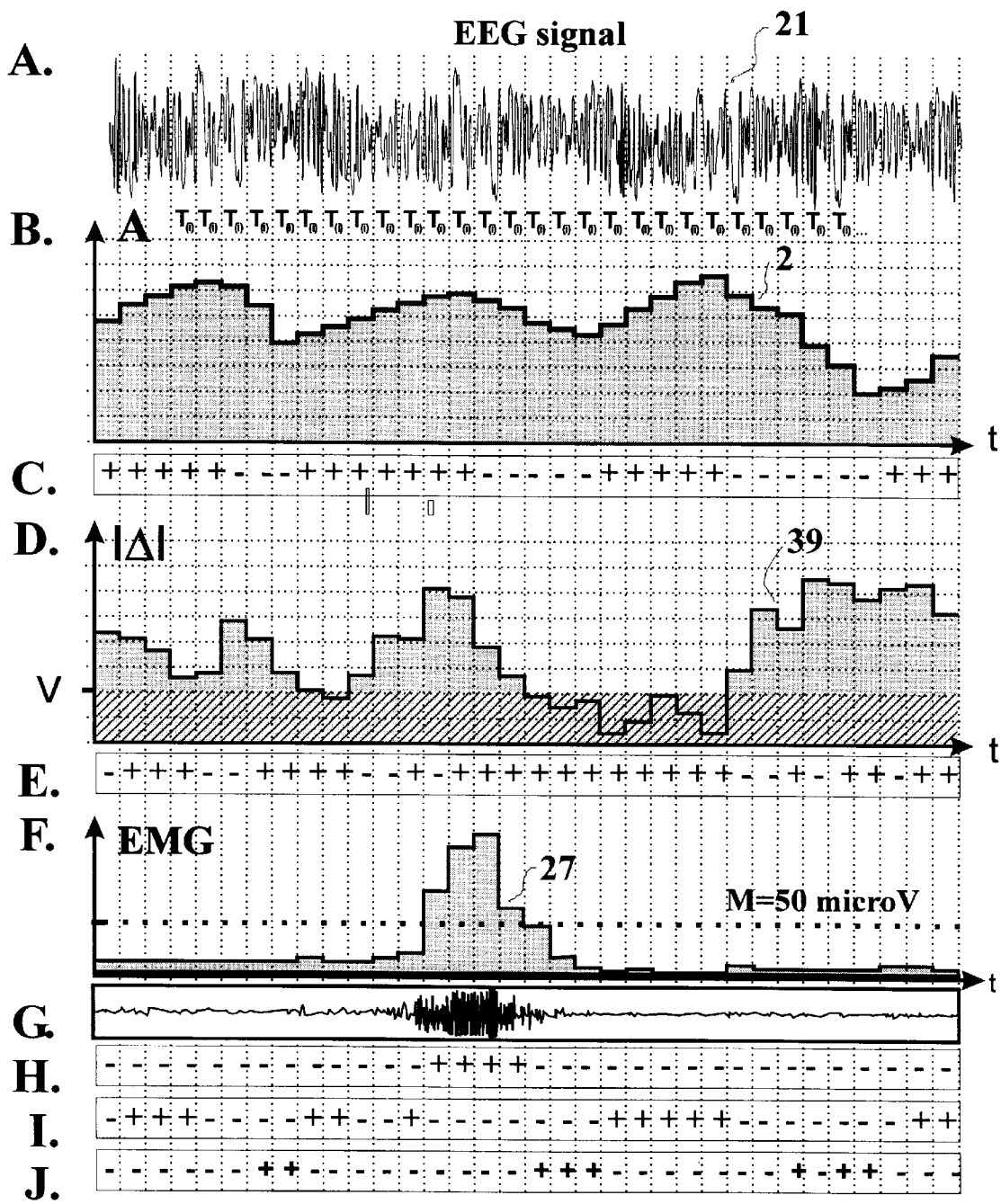
FIGS. 9A to 9J illustrate a biofeedback signal generation after signals processing during a therapeutic mode.

Simultaneously with EEG 21 and EOGs 23 and 25, the apparatus is structured to measure muscular movement of the orbicularis oculi and to record an electromyogram (EMG) 27 thereof. The EMG is used to establish any interference caused by a person blinking while using the apparatus and to factor that interference into the creation of a final triggering event. The EMG signal (shown in FIG. 9G) is processed by two half-period rectifying and low-pass filtering eliminating those frequencies below 1 Hz (FIG. 9F). The reference character M in this Figure refers to a threshold noise; 50 mV in this case. A positive signal will be established when its value is greater than the threshold noise value (M). This postive signal in the EMG corresponds to muscle movement (such as blinking or other interferences). When this is detected, the biofeedback training is blocked (stopped) for the duration of the interference (approximately 250 ns) by sending a disengaging signal to a TV 40. This helps to prevent undesired consequences of the mechanic and electric origin caused by such interferences between the EMG and EEG/EOG signals.

In operating the apparatus, a person with a known eye defect is connected to the apparatus. First this person's visual acuity, with and without optical correction, are determined. If a significant difference in the visual acuity of this person exists, then it is determined which eye is dominant and which suffers from a defect. The dominant eye having better visual acuity then is patched. This can be done by any occluding means suited for the intended purpose; preferably by which ever means is most convenient and comfortable for the person. The defect eye with a lower visual acuity then engages in a dynamic bio-feedback interaction with the apparatus. As described above, during this interaction, the function of the eye is measured, recorded, assimilated, analyzed, and by way of the bio-feedback established therefrom, a dynamic stimulus is either engaged or disengaged. This process repeats session by session, until such time, and in a suitable manner, that the defect is optically corrected to the optimum possible. If both eyes have a comparable, less than normal, visual acuity, then the person uses both eyes during the operation of and interaction with the apparatus for optimum optical correction.

The detection and the analysis of the EEG, the EOGs, and the EMG are performed as individually described and illustrated above. FIGS. 9A–9J represent the unified operation of the apparatus taking into account the EEG's, the EOG's, and the EMG's. This process is briefly summarized below. For each time period T, 37 with a lag of ⅓ second (three times per second) the analysis of all signals is performed and the biofeedback signal 72 is sent to an dynamic stimulus (such as a VCR or TV 38, 40. First, brain visual activation function A, 2 is calculated (FIG. 9B) and a trend 29 of this function is determined (FIG. 9C). Depending on the defect involved, either a positive or a negative trend may be the triggering event which engages or disengages the dynamic stimulus and, thereby, be supportive or non-supportive, respectively, of vision correction. For example, when the apparatus is used on a person with hyperopic ametropia or with astigmatism, the increase of brain visual activation function, which reflects positive trends 9 in the brain visual activation function A, 2, is supportive of correction (this is illustrated in FIG. 9C). The dynamic stimulus is thereby engaged. When the apparatus is used to treat a person with myopic ametropia, the relaxation, or negative trends 11 of the brain visual activation function A, 2 become supportive of vision correction.

If no supportive trand is established at this level, the dynamic stimulus is not engaged and the person continues his interaction with the apparatus. If the supportive trend is established at this first level of analysis, the apparatus proceeds to the analysis of Delta (Δ), 19 (shown in FIG. 9D). The trend 39 of Delta (Δ) is determined as illustrated in FIG. 9E. If this trend 39 is positive and therefore, a supportive trend, (i.e., the eye movements are becoming more synchronized), then the apparatus detects whether or not the person is blinking by way of the EMG analysis (shown in FIG. 9F). If the person is not blinking at that moment (this non-blinking activity corresponds to a "minus" mark in FIG. 9H) and is a supportive trend. An enabling biofeedback signal 72 is then generated in the computer 36 and sent to the dynamic stimulus device (such as a VCR/TV system 38/40) to engage or continue its operation. The person continues to watch a movie or to receive any other dynamic support stimuli associated with the device.

If any of these above described requirements are not met (trend of the brain visual activation function (A) is not supported, eye movements are getting less synchronized, or the person is blinking) and no supportive trend (or supporting event) is realized, then a disengaging biofeedback signal is generated and sent to the dynamic stimulus system and it is terminated. At this point, the stimulus is not enabled or is discontinued as the case may be, e.g.: TV screen fades, a movie/game stops, etc. The person's brain is encouraged by this activity and feedback to self-correct its visual function before that person is allowed to continue to engage in the pleasant activity of watching the TV or movie or playing a game.

Figure 13:
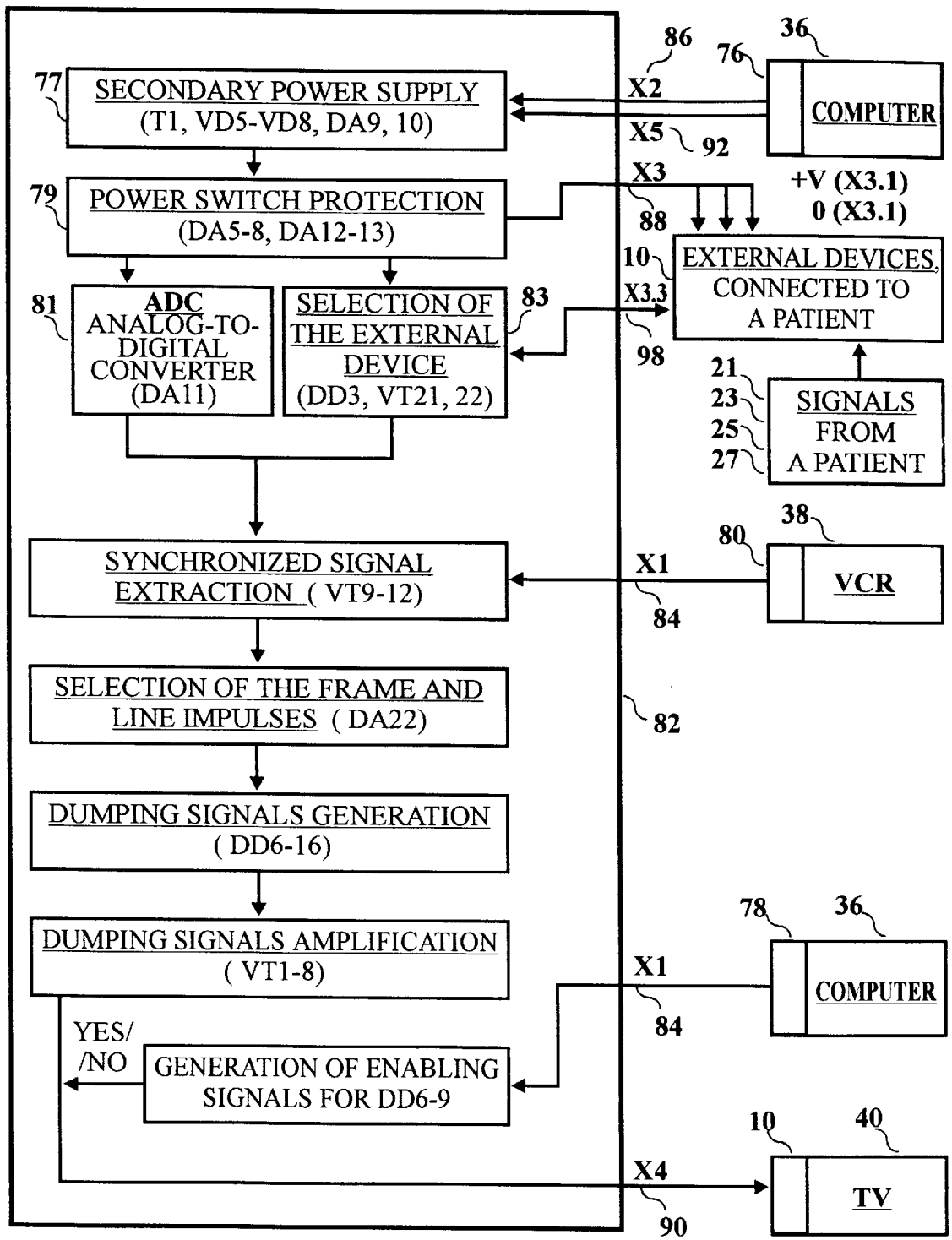
FIG. 13 is a schematic diagram showing the connections between a person and the apparatus and the signal processing operation.

All parts to construct the apparatus are standard off-the-shelf parts and components. Conventional abbreviations are used herein and in the figures. Connections between parts of the apparatus are made by connectors suited for the intended purpose and are shown in FIG. 13 in detail and described in detail herebelow. Such connectors are designated with the pre-fix "X". Signals 21, 23, 25, 27 from a person are inputted through connector X3.3 98 to an interface 82. Connection between a parallel port 78 of computer 36 and the interface 82 is realized by connector X1 84. Connector X4 90 is used to send a signal from the interface 82 to a low-frequency input 104 of, by way of example only, a TV 40. Connectors X2 86 and X5 92 are used to provide power from a computer power supply 76 to the interface circuit. Power provided by the computer power supply 76 is also used by external parts of the vision correction apparatus 102: electrodes 10, 12, 14, 16, 18, 20, 22, 24, amplifiers 28, 30, 32, 34, and electroencephalograph 26, through connector X3 88 (subparts X3.1 for ground reference, X3.2 for −V, and X3.4 for +V). For this purpose a secondary power supply 77 is formed by transformer T1, rectifiers VD5–VD8, and stabilizers DA9–DA10 (shown in detail in FIG. 11). This secondary power supply provides power to amplifiers 28, 30, 32, 34, to elements used for programmable selection of external devices 83 (comprised of DD3 and VT21–VT22), and to an analog-to-digital converter (ADC formed by element DA11) 81 in the interface (FIGS. 11 and 13). The connection between elements using the secondary power supply and the interface is realized by optoisolators DA5–DA8 and DA12–DA13, which provide an electrical switch protection up to 4 kV of direct current and up to 6 kV of alternating current. This unit is designated as a power switch protection 79 as illustrated in FIG. 14.

Signal processing is shown in FIGS. 11 and 13. The interface 82 has the following internal components and connections: output 7 of elements DD1, DD2, DD16 and DD17 is connected to a circuit GND; output 8 of elements DD4 to DD 15 is connected to a circuit GND; output 8 of an element DD3 is connected to a circuit "0"V; output 14 of elements DD1 and DD2 is connected to a circuit +5 V; output 16 of an element DD3 is connected to a circuit N; output 16 of elements DD5 to DD 15 is connected to a circuit +5 V; output 14 of elements DD4, DD 16 and DD17 is connected to a circuit +5 V. The VCR outputs signal through connector X1 84 to interface 82. The signal for synchronization is extracted on elements VT9–VT12 and then frame and line impulses are selected on the element DA22. Elements DD6–DD 16 generate dumping signals amplified by elements VT1–VT8 and directed to a TV low-frequency input 104 through connector X4 90. In this configuration, a computer 36 controls switching these dumping impulses by providing enabling signals and resetting counters of frame and line impulses DD6–DD9 through connector X1 84. Generation of the enabling/disengaging signals depends on the result of the analysis performed by a process embedded in the computer software 70 (flowcharts illustrating a typical operation of the system and apparatus are shown in FIGS. 15A to 15F).

Figure 10A:
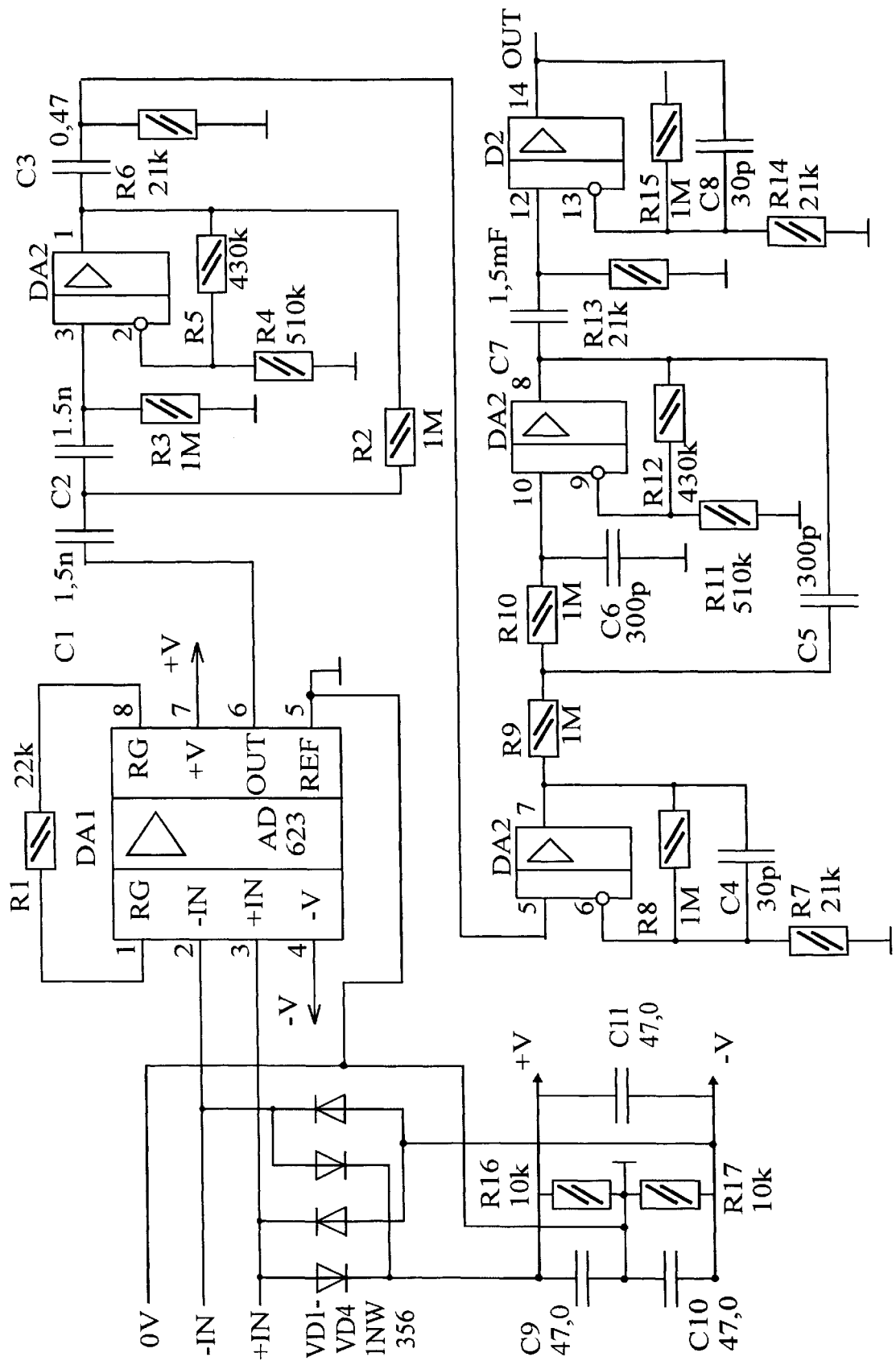
FIGS. 10A and 10B show electronic schemes for amplification of the EEG, the EOGs and the EMG signals picked up from a person's head.
Figure 10B:
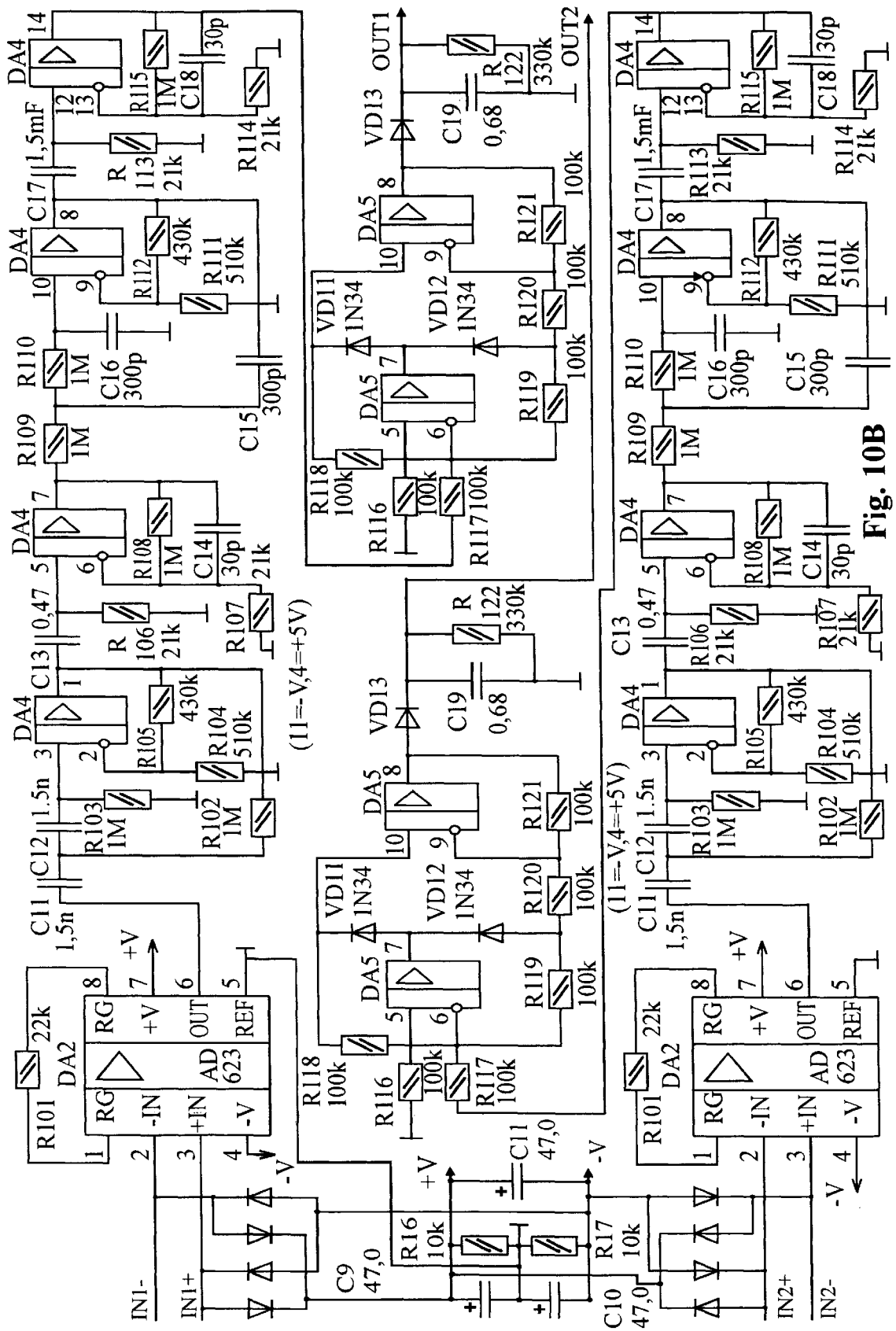
Figure 11A:
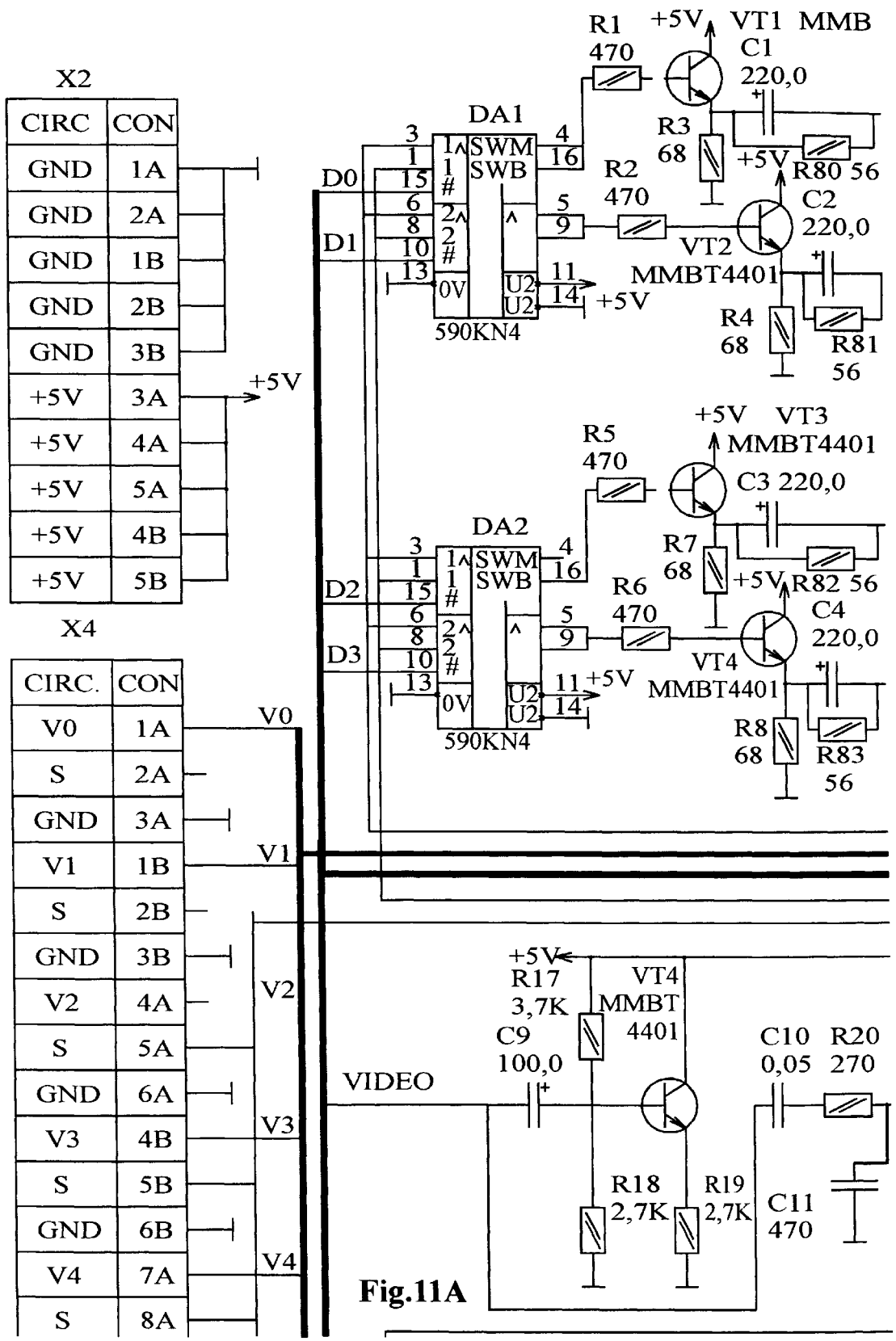
FIG. 11 shows the electronic scheme of the interface used a for computer signal processing and for a biofeedback signal generation during a biofeedback therapy session.
Figure 11B:
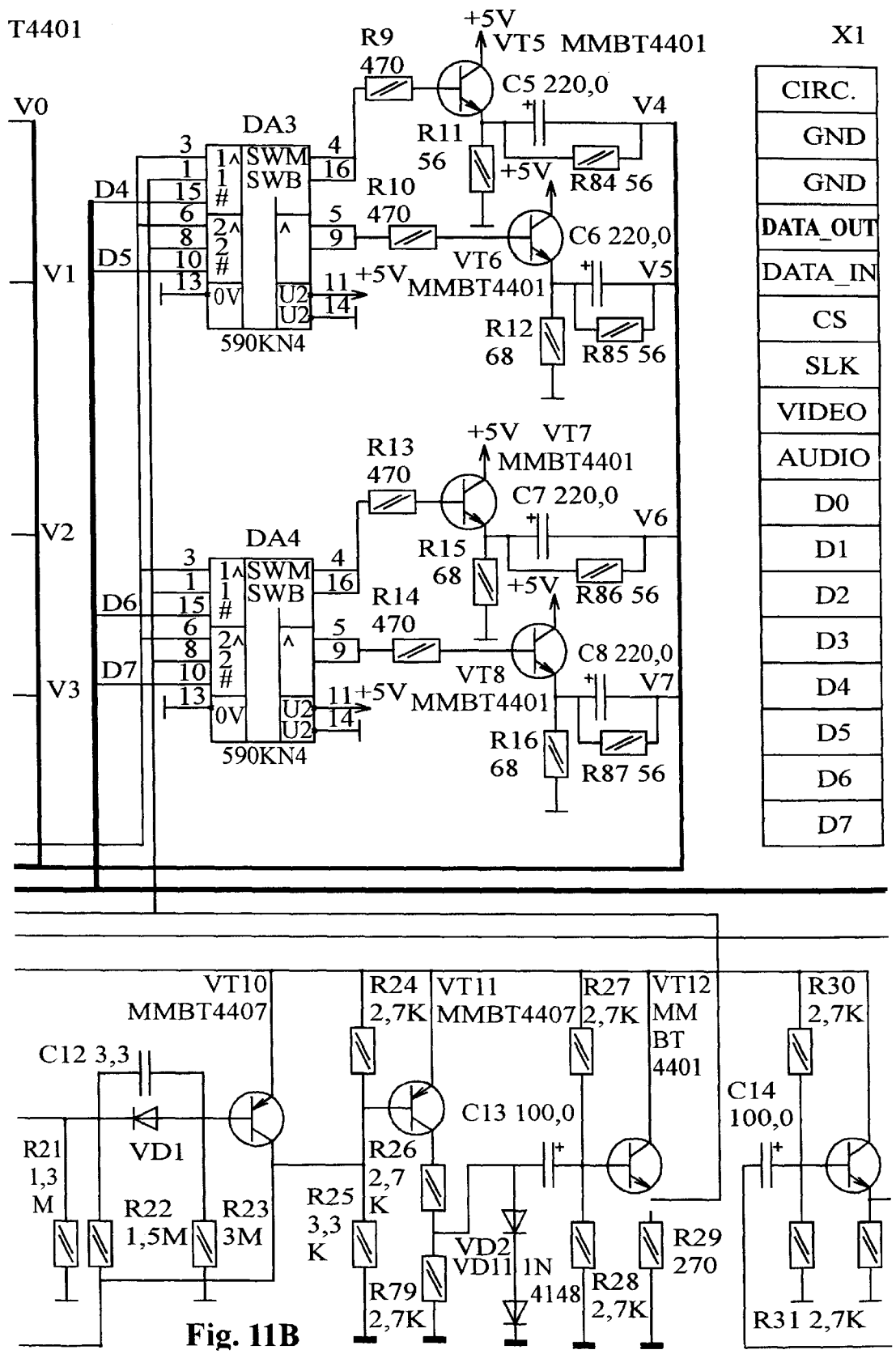
Figure 11C:
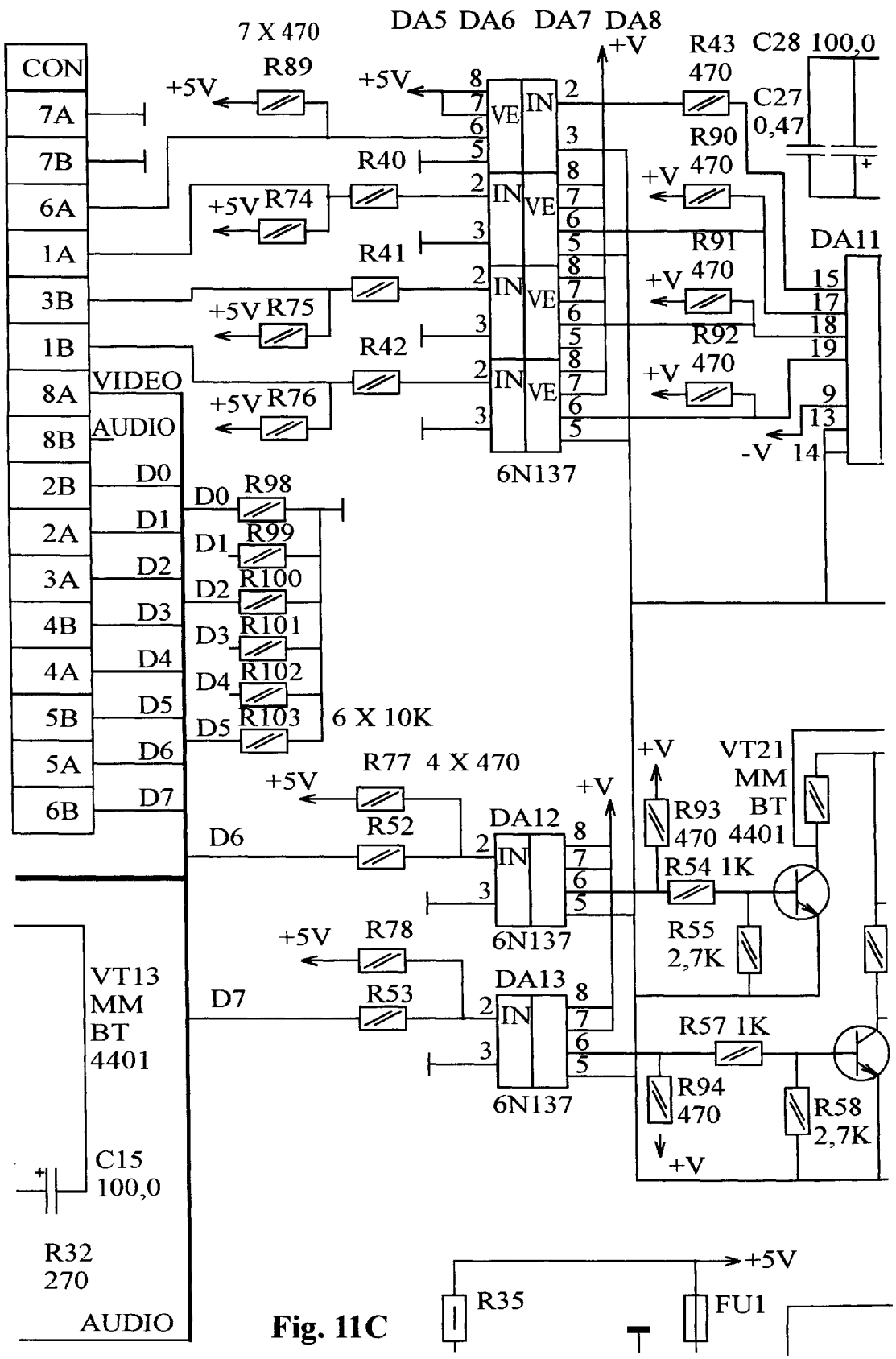
Figure 11D:
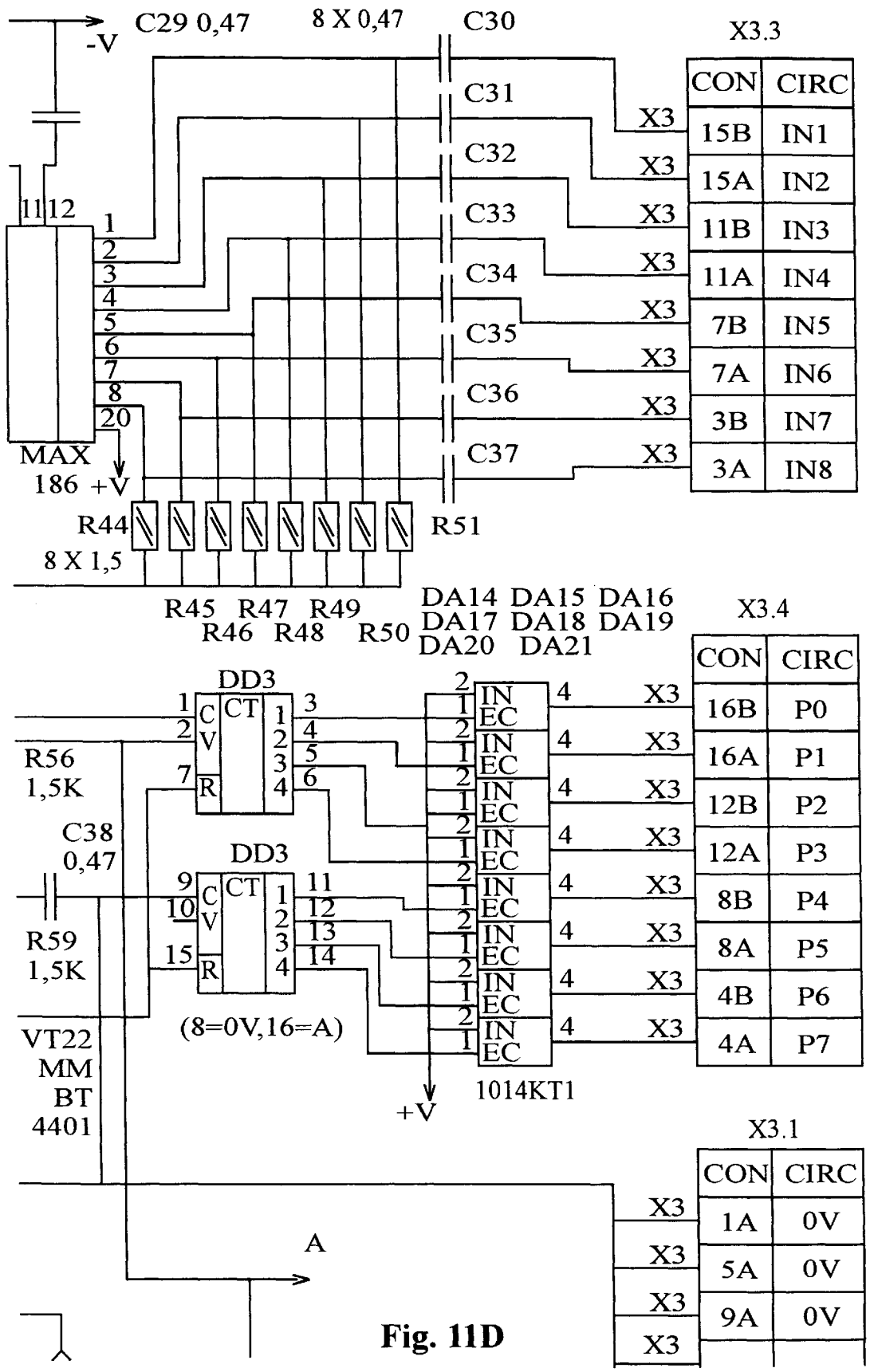
Figure 11E:
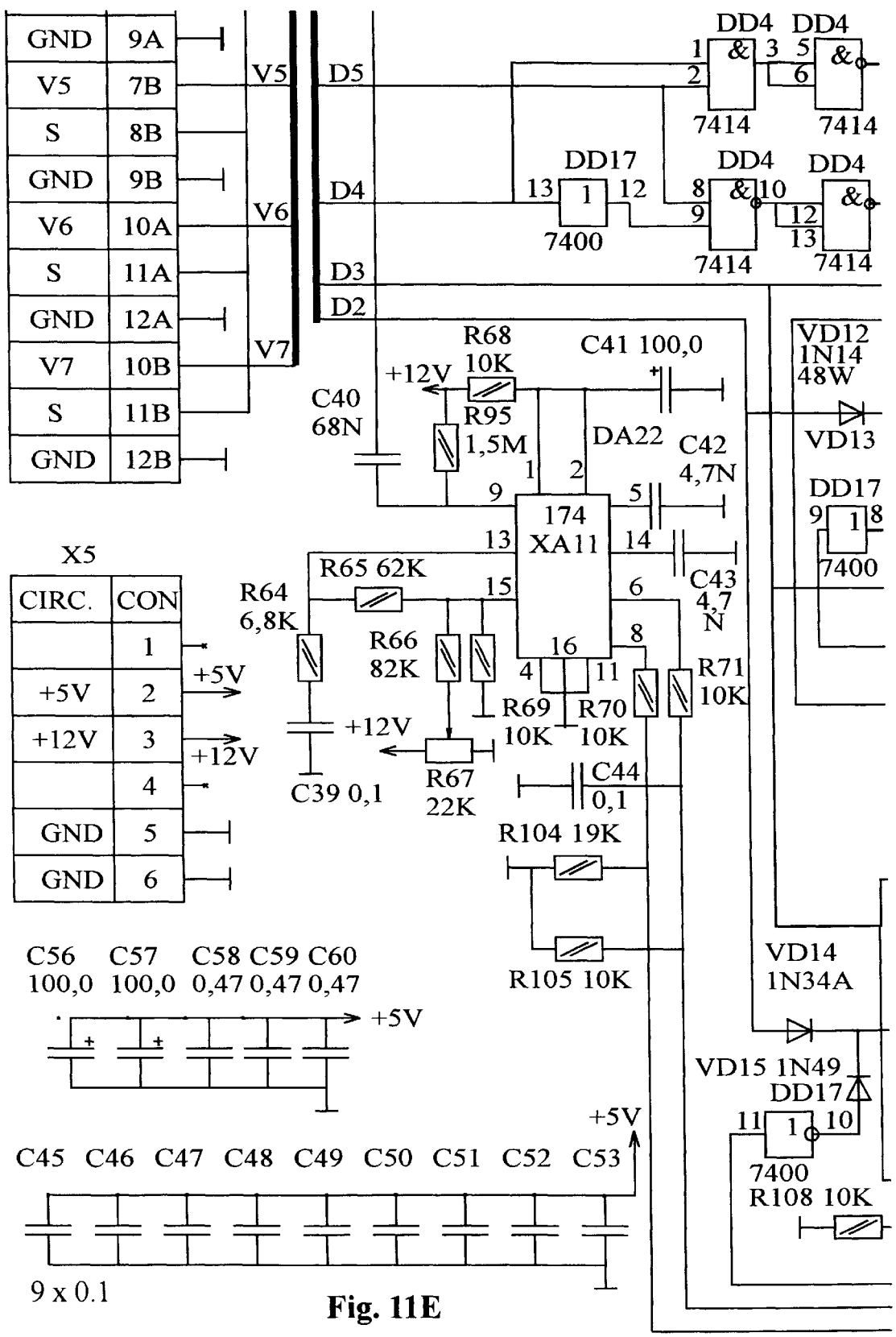
Figure 11F:
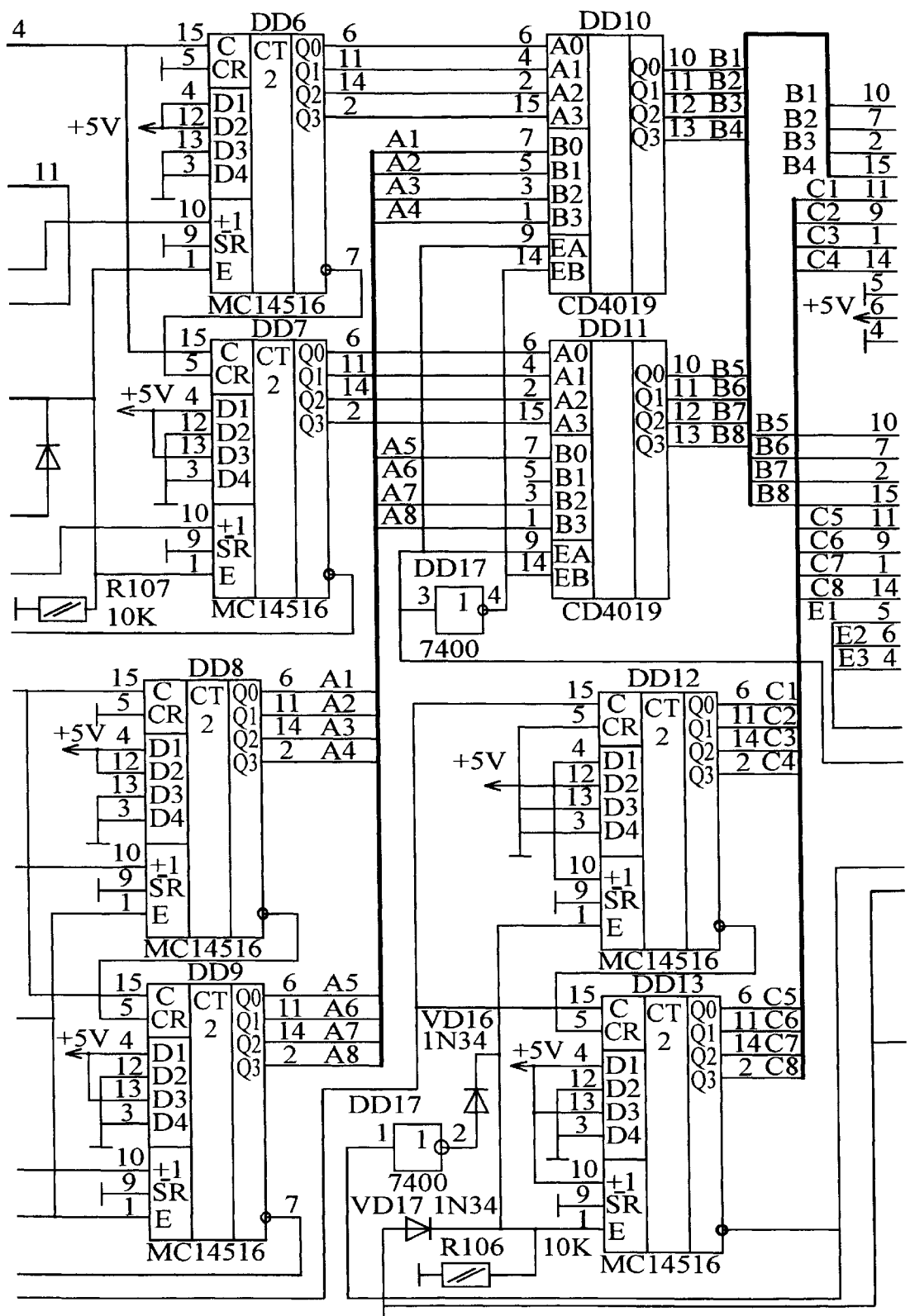
Figure 11G:
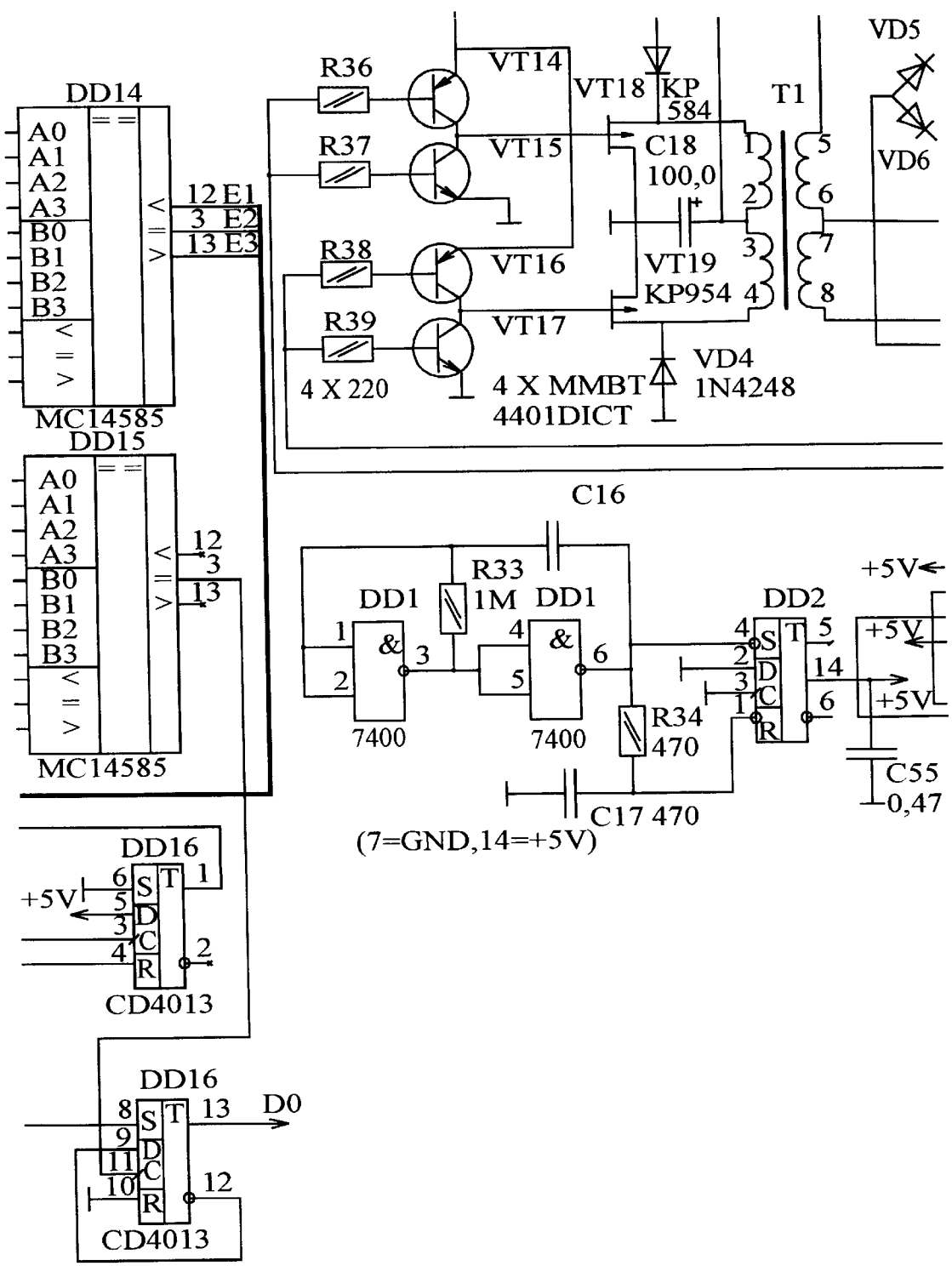
Figure 11H:
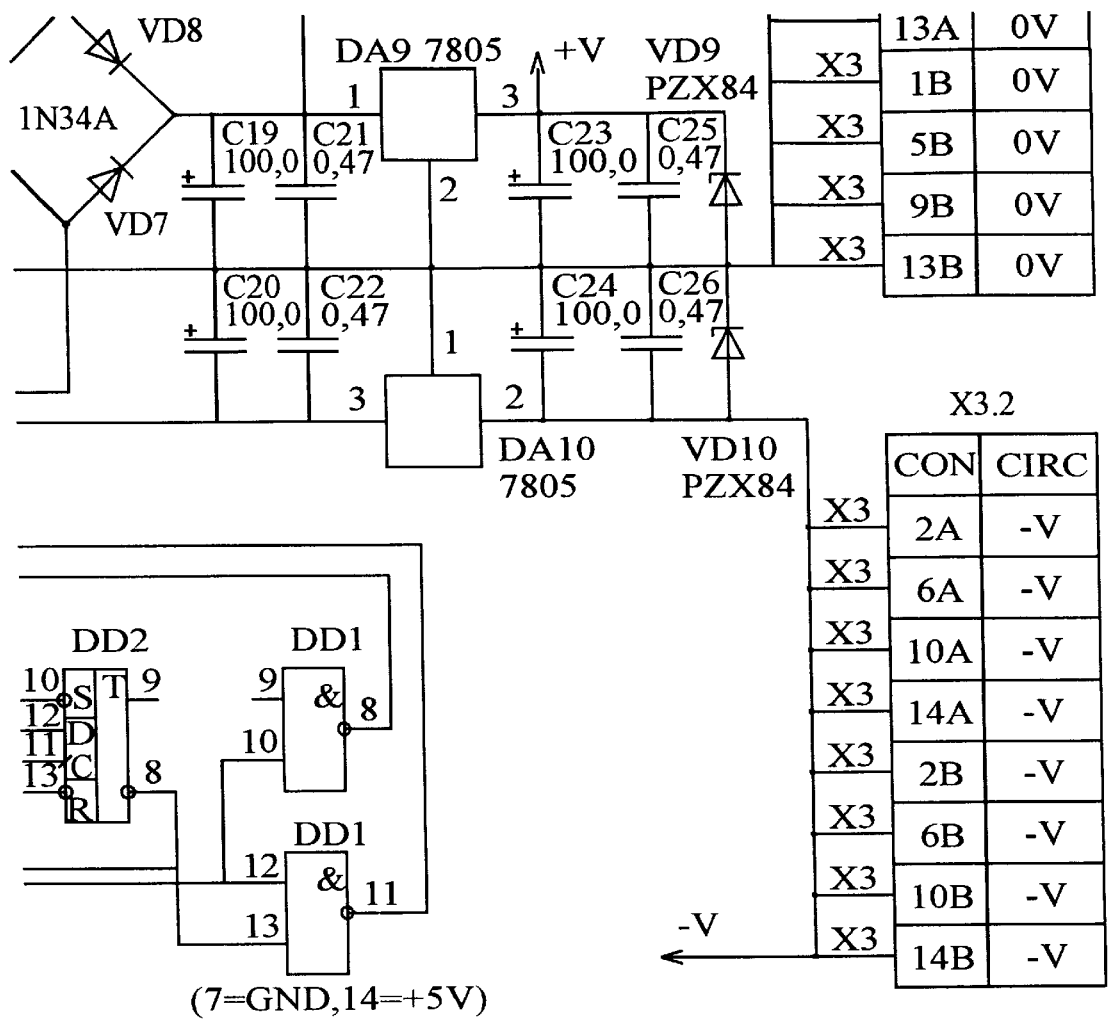

In operation, where TV and VCR are used all detecting devices, electrodes 10, 12, 14, 16, 18, 20, 22, 24 are positioned on a person's head as shown in FIG. 2. Electrodes 10, 12, 14 are used to pick up a person's brain waves EEG 21. The person uses only the defect eye (or both eyes where there is a low visual acuity in both eyes which requires correction) to view a TV 40 with dynamic support stimuli 41 coming from a VCR 38. The positioning of these electrodes is the same as those which were positioned to detect signals used to calculate a persons individual normalizing coefficients 3, 4, 5 (described above): electrode 10 touches the person's left ear; electrode 12 touches the person's right ear; electrode 14 is located on the back of the person's head 17. Electrodes 16, 18, 20 are used to detect movement function of a person's eyes (referred to previously as Delta (Δ) 19. One electrode is positioned approximately 1 cm outside of the person's left eye (electrode 16), another between the person's eyes (electrode 18), and another approximately 1 cm outside of the person's right eye (electrode 20) such that they form the line as illustrated in FIG. 2. Electrodes 22 and 24 are used to detect electromyogram (EMG) 27 of the muscle orbicularis oculi in order to determine whether or not a person is blinking. If only one eye is involved and it will be the only open eye, electrode 22 is positioned below that eye. If both eyes are to remain open, electrode 22 may be positioned below either eye. Electrode 24 is positioned above electrode 22 as shown in FIG. 2. The outputs from all electrodes pass through an electroencephalograph 26 to amplifiers 28, 30, 32, and 34 as shown in FIG. 3. The signal from electrode 14 is used as a ground reference (V=0) for all amplifiers. A first amplifier 28 inputs signals from electrodes 10 and 12 and is used to amplify the EEG signal and direct it to the computer. A second amplifier 30 inputs signals from electrodes 16 and 18 and is used to amplify the electrooculogram signal from the left eye (the EOG left). The output from the second amplifier 30 is conveyed to the computer. A third amplifier 32 inputs signals from electrodes 18 and 20. This third amplifier is used to amplify the electrooculogram signal from the right eye (the EOG right) and transmit them to the computer. A fourth amplifier 34 inputs signals from electrodes 22 and 24 and is used to amplify the electromyogram signal (EMG). The output of the fourth amplifier 34 also is transmitted to the computer 36. The schematic for the first amplifier 28 is illustrated in FIG. 1 OA; the schematic for the second, third, and fourth amplifiers 28 is illustrated in FIG. 10B.

Figure 12:
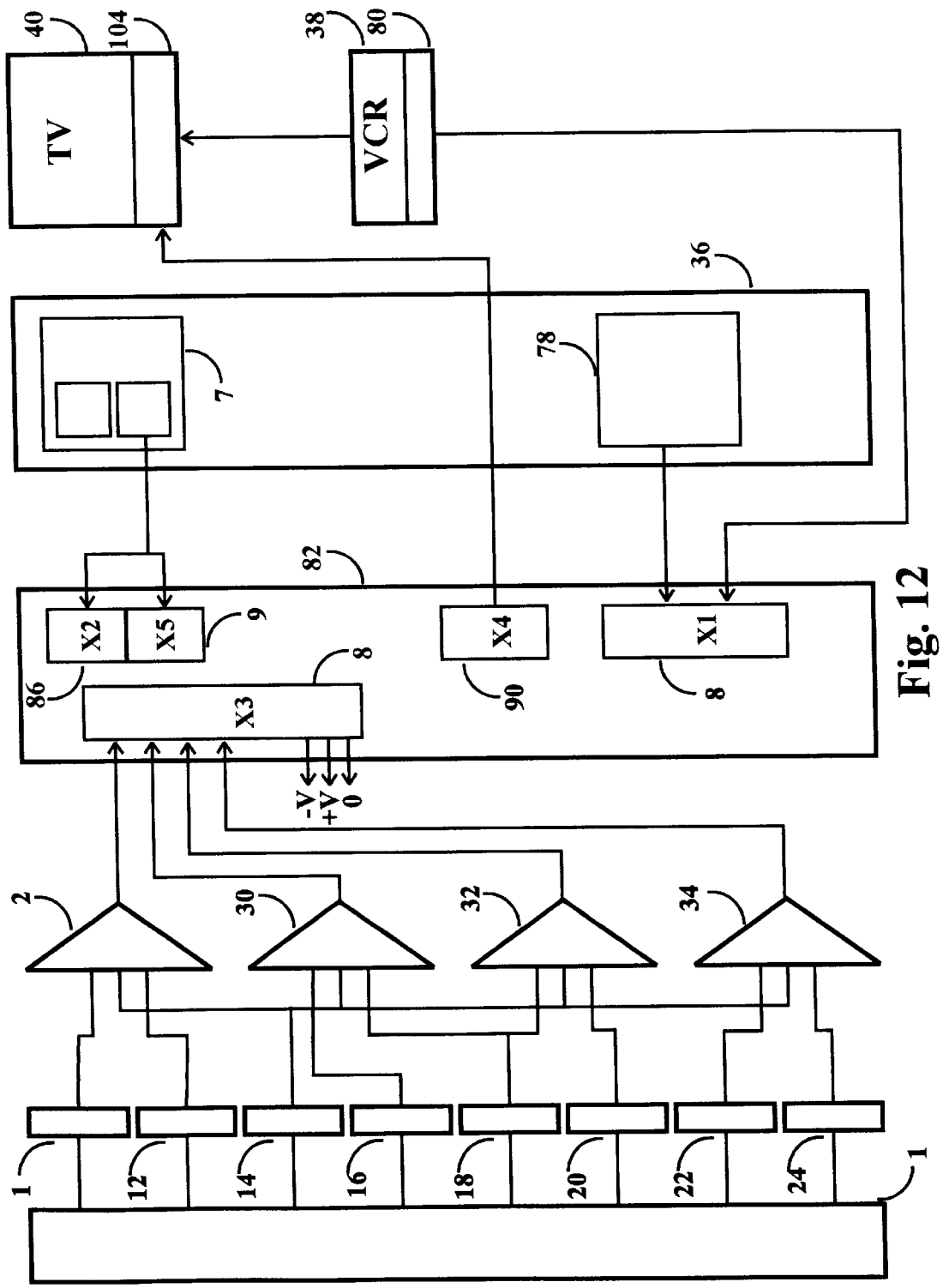
FIG. 12 is a block diagram illustrating a typical connection of the apparatus parts.

FIG. 12 illustrates the input of amplified signals 21, 23, 25, 27 picked up by electrodes 10, 12, 14, 16, 18, 20, 22, 24 through amplifiers 28, 30, 32, 34 to connector X3 88 of the interface 82 and the connections between the computer 36, the low-frequency output port 80 of a VCR 38, the low-frequency input port 104 of a TV 40, and the interface 82. The apparatus could be modified to use the high-frequency VCR output port, but that would increase the cost of the apparatus and the complexity of signal analysis.

A built-in programmable system tests all parts of the apparatus. The test includes a standard analysis of all computer parts, a test of an uploading quality from a hard-drive to RAM (random access memory) of a computer 36, an analysis of ADC 81, and a test of parameters and amplitude-frequency characteristics of the amplifiers 28, 30, 32, 34. This is a standard procedural test known to persons skilled in the art. The test is performed each time the computer 36 is booted or switched on. The apparatus will begin to function in the manner prescribed only if positive responses are obtained from the tests and analyses.

Figure 14A:
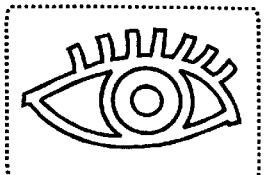
Figure 14B:
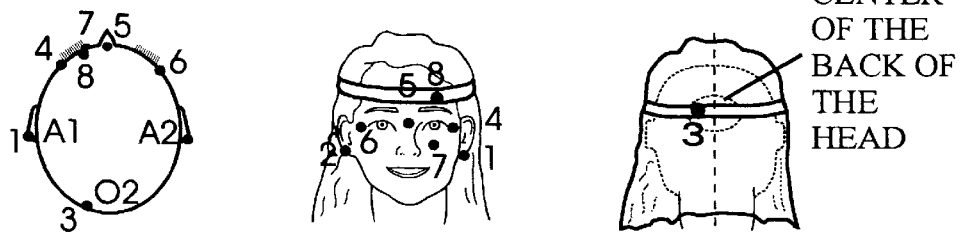
Figure 15A:
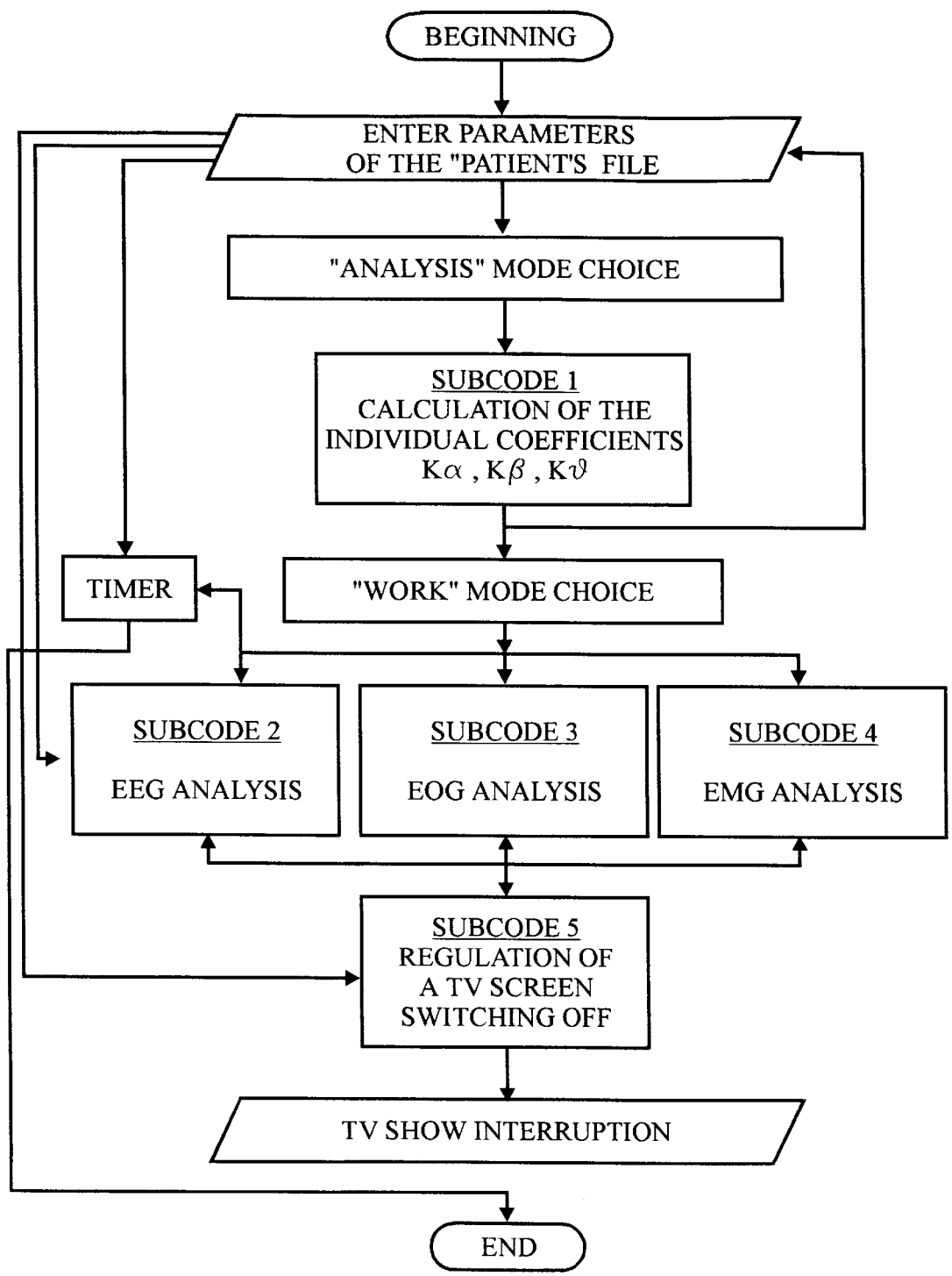
FIGS. 15A to 15F are the flowcharts of the system for signal processing and a biofeedback signal generation.
Figure 15B:
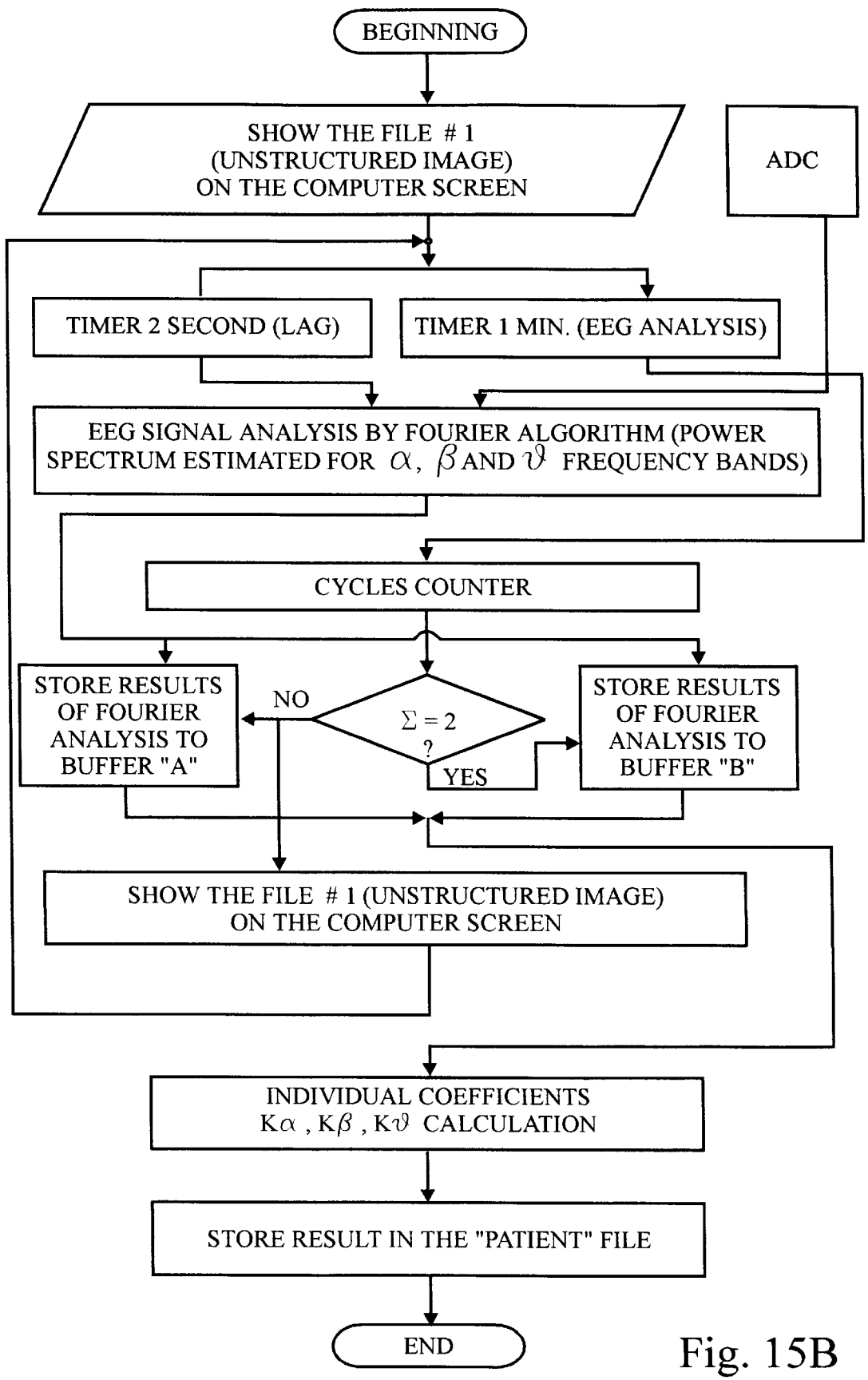
Figure 15C:
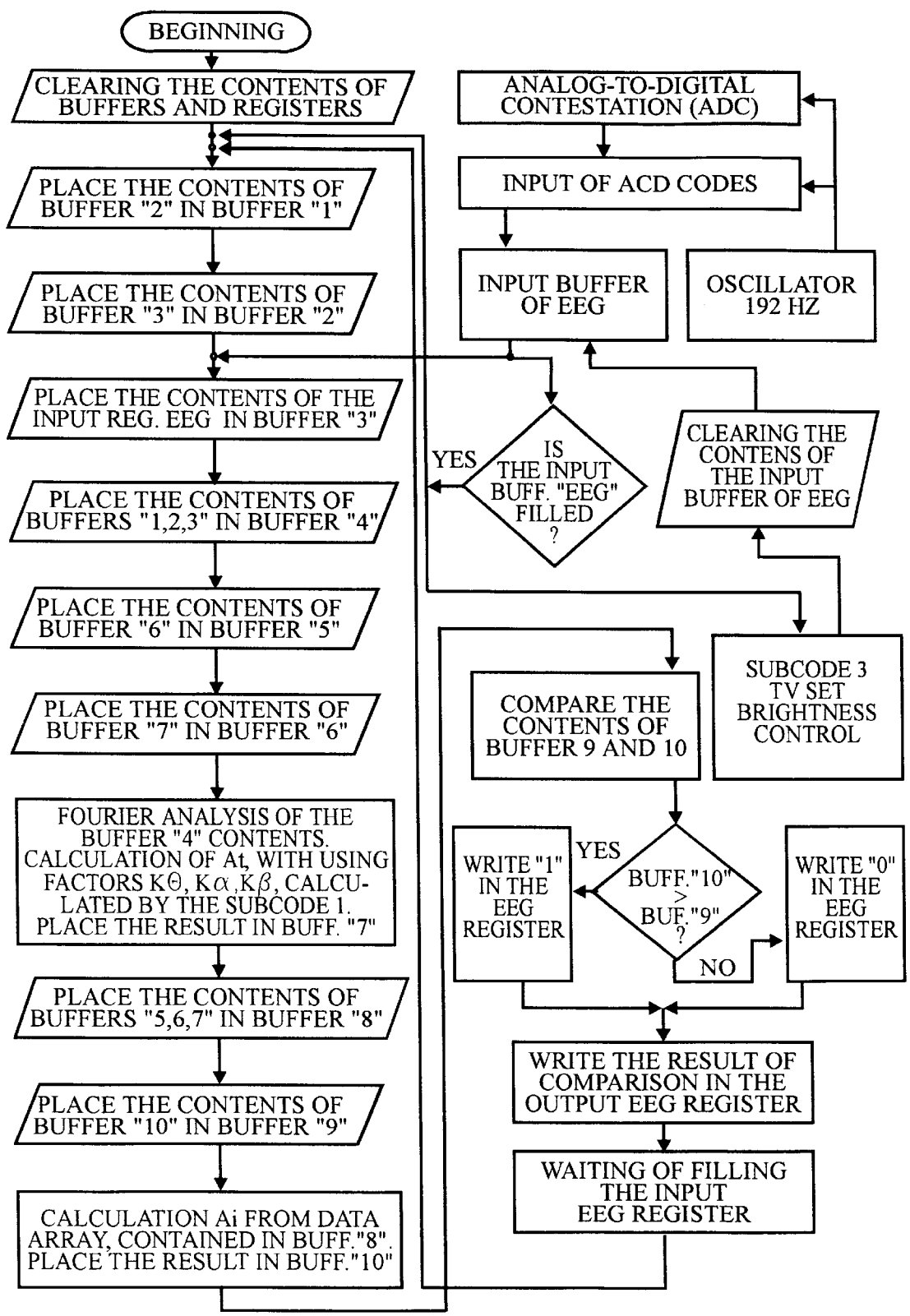
Figures 15D, 15E:
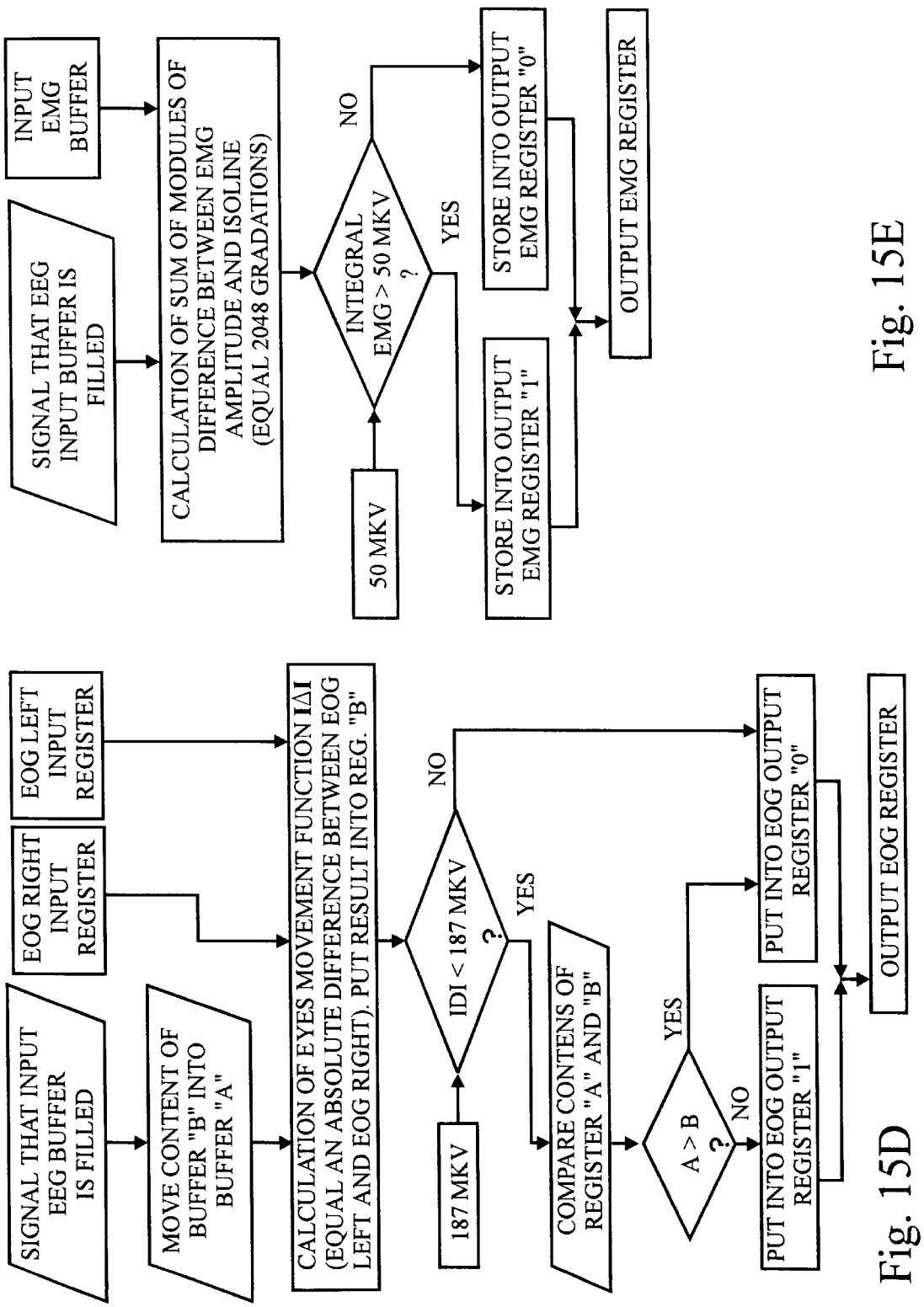
Figure 15F:
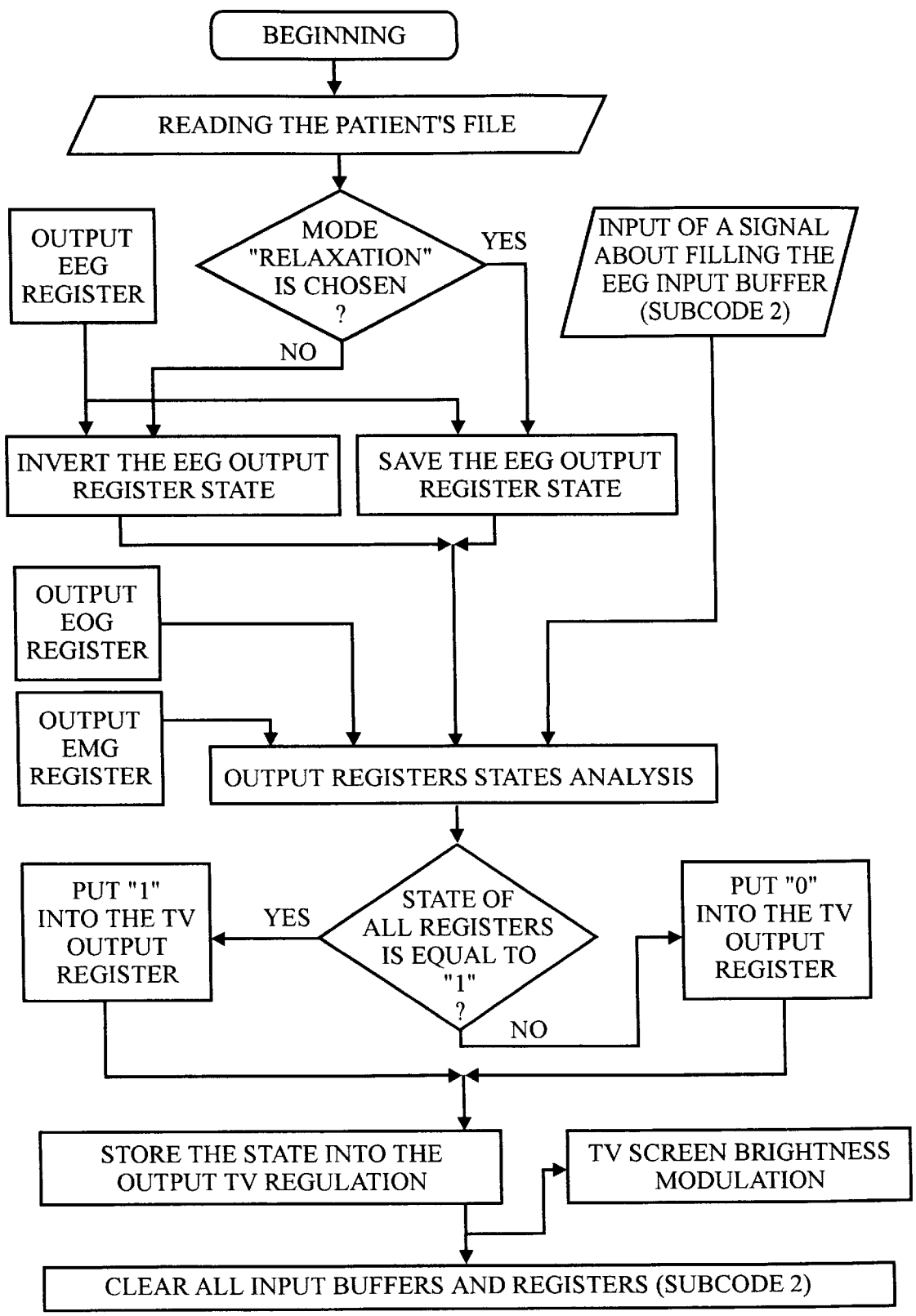

FIGS. 14A to 14D are typical display screens generated by the system during its operation. Any type screen display may be configured. The screen prompts the user for data or entry. To start the therapeutic procedure a technician performing the training session is prompted to enter the person's name, diagnosis, visual acuity parameters without optical correction, and desired optimal optic correction (shown in FIG. 14A). This is either typed in or selected from pre-existing data present in the computer memory. Positioning of electrodes 10, 12, 14, 16, 18, 20, 22, 24 on the person's head, as illustrated in FIG. 14B, is verified. A button labeled "View" allows the technician to see on the computer screen all the signals detected by these electrodes: EEG 21, EOGs 23 and 25, and EMG 27. In the case of satisfactory results the next step may begin by pushing a button labeled "Next". If the electrodes are in need of adjustment, pressing a button labeled "Cancel" stops the process and permits adjustment to be made. The next suggested step is the choice of parameters (brain visual activation function [BVAF], also referred to as individual normalizing coefficients and referenced by numerals 3, 4, 5) which are to be used during the session. FIG. 14C is representative of the screen display at this phase. In our preferred embodiment it is here where it is determined which parameters (or values) will be used for the current session; those derived during the previous session or a complete new set. The button labeled "Keep the previously used parameters" is used to choose and use the parameters collected and preserved from the previous session. At this phase the therapeutic session may commence.

The button labeled "OK" is used to derive new parameters. In this situation, the process begins anew. The user is prompted to view 11 pairs of unstructured 52 and 11 pairs of structured 54 images of the same brightness, color distribution, and size which will be displayed randomly on the TV screen for approximately 15 seconds each. Individual normalizing coefficients 3, 4, 5 are derived as described above and are stored in the computer memory. After choosing, or obtaining, the parameters, a session can be started (FIG. 14D). The user's information (such as name, optical parameters, and optical correction) is verified once again and can be corrected. The mode of the therapy ("Relaxation" or "Activation") is chosen in the window labeled "Mode" depending on the person's diagnosis. The eye position ("Right" or "Left") is shown in the window labeled "Viewing". The time of the duration of the procedure is determined in the window labeled "Time". The real time analysis of the parameters for a biofeedback signal generation appear on the screen and the session can be started by the pushing the button labeled "OK". The button labeled "Pause" will cause a session to be interrupted at any time, but does not erase any setting or value. The button labeled "Cancel" stops a session at any time. If a session is canceled, that session can be re-started from the beginning or it can be considered and used as a completed session. After the completion of the procedure, a prompt is displayed on the screen to remind the technician or the person being tested, as the case may be, to test the person's visual acuity after each session.

Conclusion, Ramifications, and Scope.

Thus it has been shown that the visual correction apparatus of the invention provides a new means to correct a person's visual acuity by training that person to improve his visual acuity and at the same time to realign the optical axes, thereby combining the benefits of both approaches. Use of the apparatus as described has no contra-indications or side effects whatsoever. It uses a modified visual function definition which is individualized and particularized for each person in order to optimize a biofeedback signal. A new approach to detect eye movements and a way to analyze oculomotor function have also been disclosed. The therapeutic procedure of using the apparatus can be performed by qualified personnel after only minimal training. It requires the use of a regular TV, a VCR, and an electroencephalograph thereby minimizing the cost of the apparatus. Furthermore, the vision correction apparatus has the additional advantages in that:

a. it trains (and thereby corrects visual acuity for) persons regardless of age, which is particularly important for preverbal children who do not understand sophisticated requirements of traditional methods (e.g., to read a table or to distinguish the pitch of a sound) and who can not respond to questions;

b. it includes an age-independent feature in describing the brain visual activity of a user which thereby facilitates treatment of persons with weakly pronounced brain alpha-waves (this is particularly problematic with young children);

c. it can be used on all persons provided a determination has been made as to the type of ametropia involved, myopic or hyperopic, a specific diagnosis is not required;

d. its is very convenient and relaxing to use and does not require a user to engage in uncomfortable activities such as maintaining one's head in a fixed position for a long period of time, requiring one to gaze at a designated point for a long period of time, or requiring one to listen to unpleasant sounds;

e. it can be used in a non-clinical setting and does not require any special facilities; and f. it provides a means of quantifying the quality of one's visual function by comparison and analysis of EEG's and EOG's during a predetermined period of time.

While the above description contains many specificities, these should not be construed as limitations on the scope of the invention, but rather as an exemplification of the presently preferred embodiment of the invention. Many other variations are possible. For example, detection of the person's EEG and classification of brainwaves can be performed by other mechanisms; amplification of signals picked up from a person can be accomplished with different electronic schemes; a separate component of an eye-movement function Delta ($\Delta$) (amplitude, direction, time) can be selected to describe the oculomotor function; a spectral analysis (Fourie analysis) can be performed with different parameters (e.g., a different time interval or time period); the biofeedback signal can be sent with a different frequency; a high frequency VCR output and/or a high-frequency TV input can be used; the interface of the apparatus can be designed other ways; processing of incoming signals and a biofeedback signal generation can be performed by different software; a variety of dynamic visual stimuli can be used; and non-visual stimuli can be used.

Accordingly, the scope of our invention should be determined not by the embodiment illustrated, but the claims which shall stem herefrom and their legal equivalents.

What is claimed is:

1. An apparatus for correcting vision of a user of said apparatus, said apparatus comprising:

a. viewing means connected to said apparatus for viewing images projected thereon;

b. a dynamic stimulus device connected to said apparatus, said dynamic stimulus device being controlled by a control signal transmitted thereto;

c. measuring means for observing and measuring viewing activity of the user, said measuring means further comprising a means for establishing a plurality of time intervals and a plurality of time periods in which observations and measurements are taken wherein each said time period comprises a plurality of time intervals;

d. data storage means for storing as data the viewing activity measured by said measuring means; and e. control means connected to said apparatus for assessing stored data in said data storage means and, in relation to an assessment made of said stored data for generating and transmitting said control signal to said dynamic stimulus device.

2. The apparatus as defined in claim 1 wherein said measuring means further comprises classifying means for classifying said alpha waves, beta waves, and theta waves into respective classified alpha waves, classified beta waves, and classified theta waves for a first viewing mode comprising the viewing a substantially unstructured image, and establishing respective classified values therefor, and for classifying said alpha waves, beta waves, and theta waves into respective classified alpha waves, classified beta waves, and classified theta waves for a second viewing mode comprising the viewing a substantially structured image, and establishing respective classified values therefor.

3. The apparatus as defined in claim 2 wherein said measuring means further comprises means for establishing individual normalizing co-efficients (INC-means), and establishing respective INC-values therefor, for said classified alpha waves between said first viewing mode and said second viewing mode (INC-alpha), for said classified beta waves between said first viewing mode and said second viewing mode (INC-beta), and for said classified theta waves between said first viewing mode and said second viewing mode (INC-theta).

4. The apparatus as defined in claim 3 further comprising a means for establishing a brain visual activation function value (BVAFV) of dynamic variances of said alpha waves between said INC-alpha value and said observed alpha value, of said beta waves between said INC-beta value and said observed beta value, and of said theta waves between said INC-theta value and said observed theta value, said BVAFV comprised of a quotient relative to a first product comprised of a product between said INC-alpha value and said observed alpha value, as said first product divisibly relates to a second product, said second product comprised of a product between a third product and a fourth product, wherein said third product is comprised of a product between said INC-theta value and said observed theta value, and said fourth product is comprised of a product between said INC-beta value and said observed beta value.

5. The apparatus as defined in claim 1 wherein said measuring means further comprises electromyogram (EMG) means for observing and measuring interfering muscular movement not associated with EOG patterns.

6. The apparatus as defined in claim 1 wherein each one of said plurality of time periods comprises at least three consecutive said time intervals.

7. The apparatus as defined in claim 6 wherein each one of said plurality of time periods overlap a previous one of said plurality of time periods by substantially two time intervals.

8. The apparatus as defined in claim 6 wherein each one of said plurality of time periods is approximately one second in duration.

9. A method of correcting vision comprising the steps of:

a. viewing as a first mode, in a pre-determined manner, at least one unstructured image;

b. viewing as a second mode, in a pre-determined manner, at least one structured image;

b. measuring EEG brain waves as alpha waves, beta waves, and theta waves, and establishing respective observed values therefor, while viewing said unstructured image and said structured image;

c. classifying said alpha waves, beta waves, and theta waves into respective classified alpha waves, classified beta waves, and classified theta waves for said first mode, and establishing respective classified values therefor, and classifying said alpha waves, beta waves, and theta waves into respective classified alpha waves, classified beta waves, and classified theta waves for said second mode, and establishing respective classified values therefor;

d. establishing individual normalizing co-efficients (INC-means) and establishing respective INC-values therefor for said classified alpha waves between said first mode and said second mode (INC-alpha), for said classified beta waves between said first mode and said second mode (INC-beta), and for said classified theta waves between said first mode and said second mode (INC-theta);

e. establishing a brain visual activation function value (BVAFV) of dynamic variances of said alpha waves between said INC-alpha value and said observed alpha value, of said beta waves between said INC-beta value and said observed beta value, and of said theta waves between said INC-theta value and said observed theta value, said BVAFV comprised of a quotient relative to a first product comprised of a product between said INC-alpha value and said observed alpha value, as said first product divisibly relates to a second product, said second product comprised of a product between a third product and a fourth product, wherein said third product is comprised of a product between said INC-theta value and said observed theta value, and said fourth product is comprised of a product between said INC-beta value and said observed beta value;

g. establishing BVAFV averages for successive time periods with each said successive time period commencing approximately one time interval after a previous time period commenced, each time period comprised of three successive time intervals of approximately one-third of a second each for a time period of approximately one second;

h. establishing a trend based on said BVAFV averages wherein if said trend is supportive an enabling control signal is transmitted to a dynamic stimulus device and if said trend is non-supportive a dis-engaging control signal is transmitted to a dynamic stimulus device; and i. enabling a dynamic stimulus device to operate thereby permitting a user to engage in the activity of said dynamic stimulus device when an enabling control signal is transmitted and dis-engaging a dynamic stimulus device from operating thereby not permitting a user to engage in the activity of said dynamic stimulus device when an disengaging control signal is transmitted.

10. The method of claim 9 further comprising the steps of observing and measuring electrooculogram (EOG) patterns and establishing absolute differences between patterns of one eye of the user and patterns of the other eye of the user over succeeding time intervals.

11. The method of claim 10 further comprising the steps of establishing a trend of EOG patterns wherein if said trend is supportive an enabling control signal is transmitted to a dynamic stimulus device and if said trend is non-supportive a dis-engaging control signal is transmitted to a dynamic stimulus device.

12. The method of claim 11 further comprising the steps of enabling a dynamic stimulus device to operate thereby permitting a user to engage in the activity of said dynamic stimulus device when an enabling control signal is transmitted and dis-engaging a dynamic stimulus device from operating thereby not permitting a user to engage in the activity of said dynamic stimulus device when an disengaging control signal is transmitted.

13. The method of claim 12 further comprising the steps of measuring a user's electromyogram (EMG) as an interfering muscular movement not associated with EOG patterns and if such an interfering muscular movement is detected, not transmitting an enabling control signal to a dynamic stimulus device.

14. An apparatus for correcting vision of a user of said apparatus, said apparatus comprising:

a. viewing means connected to said apparatus for viewing images projected thereon;

b. a dynamic stimulus device connected to said apparatus, said dynamic stimulus device being controlled by a control signal transmitted thereto;

c. measuring means for observing and measuring viewing activity of the user, said measuring means further comprising EEG means for observing and measuring EEG brain waves as alpha waves, beta waves, and theta waves, and for establishing respective observed values therefor, while viewing at least one image from said viewing means;

d. data storage means for storing as data the viewing activity measured by said measuring means; and e. control means connected to said apparatus for assessing stored data in said data storage means and, in relation to an assessment made of said stored data, for generating and transmitting said control signal to said dynamic stimulus device.

15. The apparatus as define in claim 14 wherein said measuring means further comprises classifying means for classifying said alpha waves, beta waves, and theta waves into respective classified alpha waves, classified beta waves, and classified theta waves for a first viewing mode comprising the viewing a substantially unstructured image, and establishing respective classified values therefor, and for classifying said alpha waves, beta waves, and theta waves into respective classified alpha waves, classified beta waves, and classified theta waves for a second viewing mode comprising the viewing a substantially structured image, and establishing respective classified values therefor.

16. The apparatus as defined in claim 15 wherein said measuring means further comprises means for establishing individual normalizing co-efficients (INC-means), and establishing respective INC-values therefor, for said classified alpha waves between said first viewing mode and said second viewing mode (INC-alpha), for said classified beta waves between said first viewing mode and said second viewing mode (INC-beta), and for said classified theta waves between said first viewing mode and said second viewing mode (INC-theta).

17. The apparatus as defined in claim 16 further comprising a means for establishing a brain visual activation function value (BVAFV) of dynamic variances of said alpha waves between said INC-alpha value and said observed alpha value, of said beta waves between said INC-beta value and said observed beta value, and of said theta waves between said INC-theta value and said observed theta value, said BVAFV comprised of a quotient relative to a first product comprised of a product between said INC-alpha value and said observed alpha value, as said first product divisibly relates to a second product, said second product comprised of a product between a third product and a fourth product, wherein said third product is comprised of a product between said INC-theta value and said observed theta value, and said fourth product is comprised of a product between said INC-beta value and said observed beta value.

18. The apparatus as defined in claim 14 wherein said measuring means further comprises electrooculogram (EOG) means for observing and measuring EOG patterns and establishing absolute differences between patterns of one eye of the user and patterns of the other eye of the user over succeeding time intervals.

19. The apparatus as defined in claim 18 wherein said measuring means further comprises electromyogram (EMG)

means for observing and measuring interfering muscular movement not associated with EOG patterns.

20. The apparatus as defined in claim 14 wherein said measuring means further comprises a means for establishing a plurality of time intervals and a plurality of time periods in which observations and measurements are taken wherein said time period comprises a plurality of time intervals.

21. The apparatus as defined in claim 20 wherein each one of said plurality of time periods comprises at least three consecutive said time intervals.

22. The apparatus as defined in claim 21 wherein each one of said plurality of time periods overlap a previous one of said plurality of time periods by substantially two time intervals.

23. The apparatus as defined in claim 22 wherein each one of said plurality of time periods is approximately one second in duration.

24. An apparatus for correcting vision of a user of said apparatus, said apparatus comprising:

a. viewing means connected to said apparatus for viewing images projected thereon;
   b. a dynamic stimulus device connected to said apparatus, said dynamic stimulus device being controlled by a control signal transmitted thereto;
   c. measuring means for observing and measuring viewing activity of the user, said measuring means further comprising electrooculogram (EOG) means for observing and measuring EOG patterns and establishing absolute differences between patterns of one eye of the user and patterns of the other eye of the user over succeeding time intervals;
   d. data storage means for storing as data the viewing activity measured by said measuring means; and
   e. control means connected to said apparatus for assessing stored data in said data storage means and, in relation to an assessment made of said stored data, for generating and transmitting said control signal to said dynamic stimulus device.

25. The apparatus as defined in claim 24 wherein said measuring means further comprises EEG means for observing and measuring EEG brain waves as alpha waves, beta waves, and theta waves, and for establishing respective observed values therefor, while viewing at least one image from said viewing means.

26. The apparatus as defined in claim 25 wherein said measuring means further comprises classifying means for classifying said alpha waves, beta waves, and theta waves into respective classified alpha waves, classified beta waves, and classified theta waves for a first viewing mode comprising the viewing a substantially unstructured image, and establishing respective classified values therefor, and for classifying said alpha waves, beta waves, and theta waves into respective classified alpha waves, classified beta waves, and classified theta waves for a second viewing mode comprising the viewing a substantially structured image, and establishing respective classified values therefor.

27. The apparatus as defined in claim 26 wherein said measuring means further comprises means for establishing individual normalizing co-efficients (INC-means), and establishing respective INC-values therefor, for said classified alpha waves between said first viewing mode and said second viewing mode (INC-alpha), for said classified beta waves between said first viewing mode and said second viewing mode (INC-beta), and for said classified theta waves between said first viewing mode and said second viewing mode (INC-theta).

28. The apparatus as defined in claim 27 means for establishing a brain visual activation function value (BVAFV) of dynamic variances of said alpha waves between said INC-alpha value and said observed alpha value, of said beta waves between said INC-beta value and said observed beta value, and of said theta waves between said INC-theta value and said observed theta value, said BVAFV comprised of a quotient relative to a first product comprised of a product between said INC-alpha value and said observed alpha value, as said first product divisibly relates to a second product, said second product comprised of a product between a third product and a fourth product, wherein said third product is comprised of a product between said INC-theta value and said observed theta value, and said fourth product is comprised of a product between said INC-beta value and said observed beta value.

29. The apparatus as defined in claim 24 means further comprises electromyogram (EMG) means for observing and measuring interfering muscular movement not associated with EOG patterns.

30. The apparatus as defined in claim 24 wherein said measuring means further comprises a means for establishing a plurality of time intervals and a plurality of time periods in which observations and measurements are taken wherein each said time period comprises a plurality of time intervals.

31. The apparatus as defined in claim 30 wherein each one of said plurality of time periods comprises at least three consecutive said time intervals.

32. The apparatus as defined in claim 31 wherein each one of said plurality of time periods overlap a previous one of said plurality of time periods by substantially two time intervals.

33. The apparatus as defined in claim 31 wherein each one of said plurality of time periods is approximately one second in duration.

* * * * *